(12) United States Patent
    Bastarrachea

(10) Patent No.:    US 12,616,735 B2
(45) Date of Patent:      May 5, 2026

(54) COMPOSITIONS AND METHODS OF CONTROLLING EXPRESSION OF THERMOGENIN (UCP-1) IN SKELETAL MUSCLES

(71) Applicant: Raul Bastarrachea, Houston, TX (US)

(72) Inventor: Raul Bastarrachea, Houston, TX (US)

(73) Assignee: Raul Bastarrachea, Houston, TX (US)

( * ) Notice:    Subject to any disclaimer, the term of this patent is extended or adjusted under 35 U.S.C. 154(b) by 919 days.

(21) Appl. No.: 16/502,509

(22) Filed:    Jul. 3, 2019

(65)         Prior Publication Data

US 2020/0009227 A1     Jan. 9, 2020

Related U.S. Application Data

(60) Provisional application No. 62/693,775, filed on Jul. 3, 2018.

(51) Int. Cl.

| | |
|---|---|
| *A61K 38/18* | (2006.01) |
| *A61K 9/127* | (2025.01) |
| *A61K 38/17* | (2006.01) |
| *A61K 47/06* | (2006.01) |
| *A61K 48/00* | (2006.01) |
| *A61K 49/22* | (2006.01) |
| *C12N 15/85* | (2006.01) |

(52) U.S. Cl.
CPC .......... *A61K 38/1841* (2013.01); *A61K 9/127* (2013.01); *A61K 38/1709* (2013.01); *A61K 38/1875* (2013.01); *A61K 47/06* (2013.01); *A61K 48/0041* (2013.01); *A61K 49/223* (2013.01); *C12N 15/85* (2013.01)

(58) Field of Classification Search
CPC ............ A61K 38/1841; A61K 38/1709; A61K 38/1875; A61K 48/0041; A61K 49/223; C12N 15/85
See application file for complete search history.

(56)         References Cited

U.S. PATENT DOCUMENTS

| | | | | |
|---|---|---|---|---|
| 2007/0243177 | A1 * | 10/2007 | Newgard | ............... C07K 14/47 |
| | | | | 435/375 |
| 2013/0331433 | A1 * | 12/2013 | Thibonnier | .......... C12Q 1/6883 |
| | | | | 435/375 |

FOREIGN PATENT DOCUMENTS

WO    WO-2007008220 A2 *   1/2007   ......... A61K 41/0028

OTHER PUBLICATIONS

Bastarrachea et al., Engineering Brown Fat into Skeletal Muscle Using Ultrasound-Targeted Microbubble Destruction Gene Delivery in Obese Zucker Rats: Proof of Concept Design, Jul. 31, 2017, IUBMB Life, vol. 69, No. 9, pp. 745-755 (Year: 2017).*

Chen et al., Successful β cells islet regeneration in streptozotocin-induced diabetic baboons using ultrasound-targeted microbubble gene therapy with cyclinD2/CDK4/GLP1, 2014, Cell Cycle, vol. 13, Issue 7, pp. 1145-1151 (Year: 2014).*

Svensson et al., Gene expression in human brown adipose tissue, 2011, International Journal of Molecular Medicine, vol. 27, pp. 227-232 (Year: 2011).*

Becerril et al., Role of PRDM16 in the activation of brown fat programming. Relevence to the development of obesity, 2013, Histology and Histopathology, vol. 28, pp. 1411-1425 (Year: 2013).*

Tseng et al., New role of bone morphogenetic protein 7 in brown adipogenesis and energy expenditure, 2008, Nature, vol. 454, Issue 7207, pp. 1-16 (Year: 2008).*

Zhang et al., Enhanced Gene Delivery into Skeletal Muscles with Ultrasound and Microbubble Techniques, 2006, Academic Radiology, vol. 13, Issue 3, pp. 1-4 (Year: 2006).*

Sharma et al., Negative Regulators of Brown Adipose Tissue (BAT)-Mediated Thermogenesis, 2014, Journal of Cell Physiology, vol. 229, Issue 12, pp. 1901-1907 (Year: 2014).*

Yusa et al., A hyperactive piggyBac transposase for mammalian applications, 2011, PNAS, vol. 108, No. 4, pp. 1531-1536 (Year: 2011).*

Bastarrachea et al., Engineering Brown Fat into Skeletal Muscle Using Ultrasound-Targeted Microbubble Destruction Gene Delivery in Obese Zucker Rats: Proof of Concept Design, 2017 International Union of Biochemistry and Molecular Biology, vol. 69, No. 9, Sep. 2017, pp. 745-755.

* cited by examiner

*Primary Examiner* — Jeffrey Stucker
*Assistant Examiner* — Brittney E Donoghue
(74) *Attorney, Agent, or Firm* — Womble Bond Dickinson (US) LLP

(57)         ABSTRACT

Described herein are pharmaceutical compositions containing genes encoding a positive regulatory domain zinc finger protein 16, a peroxisome proliferator-activated receptor gamma coactivator 1-alpha protein, and a bone morphogenetic protein 7. Also disclosed are methods of treating or managing obesity and diabetes by delivering these pharmaceutical compositions using ultrasound-targeted microbubble destruction.

8 Claims, 34 Drawing Sheets
(21 of 34 Drawing Sheet(s) Filed in Color)

COMPOSITIONS AND METHODS OF CONTROLLING EXPRESSION OF THERMOGENIN (UCP-1) IN SKELETAL MUSCLES

RELATED APPLICATION

This application is claiming priority to and the benefit of U.S. Provisional Application Ser. No. 62/693,775 filed on Jul. 3, 2018, which is incorporated by reference in its entirety.

TECHNICAL FIELD

This disclosure relates to compositions and methods for managing obesity by controlling expression of mitochondrial uncoupling proteins in skeletal muscles of a mammalian subject.

BACKGROUND

Obesity is a common, complex, highly prevalent disorder currently affecting more than a third of the world's population. Obesity is closely associated with multiple metabolic disturbances including cardiometabolic diseases. Diet, exercise and behavior modifications remain the current cornerstones of obesity treatment and prevention, even though they work very poorly for successful long-term weight loss. Therefore, there is a desperate need of powerful strategies for the treatment of obesity to achieve long-term weight loss and maintenance. Brown adipose tissue is the main organ of adaptive nonshivering thermogenesis in humans. Brown adipocytes have a high mitochondrial content that contains a specialized protein—mitochondrial uncoupling protein (mUCP-1). This specialized protein uncouples ATP production from mitochondrial respiration and converts energy into heat. Gene therapy utilize both viral vectors and non-viral gene therapy. Non-viral gene delivery mechanisms are advantageous for certain diseases without potential complications of toxicity, altered immune response, and decreased capability to target specific cells. The focus of obesity-related gene therapy is to favor energy expenditure and lipolysis by modulating expression of appropriate gene targets to restore and maintain energy homeostasis. Ectopic expression of UCP-1 in skeletal muscles of transgenic mice has been shown to result in a phenotype characterized by increased energy expenditure, reduced body weight, reduced fat mass, improved glucose tolerance, decreased muscle energy efficiency, and altered substrate oxidation, as well as increased longevity. However, the usefulness of transgenic mice in determining the precise functional roles of cloned genes is limited by several technical factors such as variability in the copy number of transgenes inserted and potential functional alterations of neighboring cells. Random integration of transgenes within the genome is particularly worrisome. In theory, once integrated into the murine genome of transgenic mice, the injected DNA can manifest its function. However, as the insertion occurs at random, positional variegation or cell mutation effects may be considered, and both the function of endogenous genes might be affected by the insertion of a transgene as well as the expression of the transgene itself may also be severely compromised by surrounding elements.

Delivery of adenoviruses containing cDNA of UCP-1 to the epididymal fat pads in mice induced localized fat depletion, improved glucose tolerance and decreased food intake in obese diabetic mice. However, there are disadvantages with the utilization of adenovirus vectors. As adenoviruses are non-integrating viruses, the transgene expression typically lasts about one to two months in non-dividing cells, and the expression time frame is much shorter in dividing cells. Therefore, transfer and expression are transient. Pre-existing immunity against adenoviruses in individuals may result in low levels of transgene delivery and expression. Viral vectors are immunogenic because the virus capsid and remaining viral proteins cause inflammation. In certain instances, adenovirus vectors cause patient death through their systemic delivery by triggering a massive inflammatory response that leads to disseminated intravascular coagulation and multi-organ failure. New strategies for weight loss treatment and prevention of obesity-related comorbidities are needed to successfully reverse or prevent the health complications caused by fat accumulation.

SUMMARY

Disclosed herein are compositions and methods addressing the shortcomings of the art, and may provide any number of additional or alternative advantages, including controlled expression of mitochondrial uncoupling proteins in skeletal muscles of a mammalian subject.

Disclosed here are pharmaceutical compositions containing nucleic acid constructs coding PRDM16 (Positive Regulatory Domain Zinc Finger Protein 16), PPARGC-1α (Peroxisome proliferator-activated receptor gamma coactivator 1-alpha), and BMP7 (Bone morphogenetic protein 7). Also disclosed here are methods of delivery of the nucleic acid compositions containing expression cassettes coding PRDM16, PPARGC-1α, and BMP7 to skeletal muscle of a subject using a plurality of non-viral vectors and ultrasound-targeted microbubble destruction (UTMD) techniques. Also disclosed here are methods of delivery of the nucleic acid compositions containing expression cassettes coding PRDM16, PPARGC-1α, and BMP7 to skeletal muscle of a subject for the treatment of obesity. Also disclosed here are methods of delivery of the nucleic acid compositions containing expression cassettes coding PRDM16, PPARGC-1α, and BMP7 to skeletal muscle of a subject for management of diabetes.

In an embodiment, the pharmaceutical composition contains three non-viral nucleic acid constructs. The first non-viral nucleic acid construct contains a first expression cassette encoding a positive regulatory domain zinc finger protein 16. The second non-viral nucleic acid construct contains a second expression cassette encoding a peroxisome proliferator-activated receptor gamma coactivator 1-alpha protein. And, the third non-viral nucleic acid construct contains a third expression cassette encoding a bone morphogenetic protein 7. In certain embodiments, the pharmaceutical composition is a microbubble suspension formed by mixing a plurality of lipids with a mixture of the first non-viral nucleic acid construct, the second nucleic acid construct, and the third nucleic acid construct. In certain embodiments, the pharmaceutical composition is a microbubble suspension of lipid-coated microbubbles containing a gas suitable for ultrasound-targeted microbubble destruction and a mixture of the first non-viral nucleic acid construct, the second nucleic acid construct, and the third nucleic acid construct. In certain embodiments, the gas is perfluoropropane. In certain embodiments, the plurality of lipids is a plurality of cationic lipids. For example, the plurality of lipids can include 1,2-dipalmitoyl-sn-glycero-3-phosphatidylcholine and 1,2-dipalmitoyl-sn-glycero-3-phosphatidyl ethanolamine.

Also disclosed here are methods of treating obesity in a mammal. One such method includes the steps of providing a microbubble suspension containing a first non-viral nucleic acid construct with a first expression cassette encoding a positive regulatory domain zinc finger protein 16, a second non-viral nucleic acid construct with a second expression cassette encoding a peroxisome proliferator-activated receptor gamma coactivator 1-alpha protein, and a third non-viral nucleic acid construct with a third expression cassette encoding a bone morphogenetic protein 7. The microbubble suspension is introduced into a target cell of the mammal in vivo and then, the target cell is exposed to ultrasound waves to release the first non-viral nucleic acid construct, the second nucleic acid construct, and the third nucleic acid construct. The first non-viral nucleic acid construct is expressed by the target cell to provide the positive regulatory domain zinc finger protein 16, the second nucleic acid construct is expressed by the target cell to provide the peroxisome proliferator-activated receptor gamma coactivator 1-alpha protein, and the third nucleic acid construct is expressed by the target cell to provide the bone morphogenetic protein 7 at levels sufficient to increase expression of mitochondrial uncoupling protein in the target cell. The target cell can be a skeletal muscle cell. In certain embodiments, the target cell is exposed to ultrasound waves applied in an ultraharmonic mode. In certain embodiments, the microbubble suspension is formed by mixing the first non-viral nucleic acid construct, the second non-viral nucleic acid construct, and a third non-viral nucleic acid construct with a plurality of lipids and a gas suitable for ultrasound-targeted microbubble destruction. In certain embodiments, the gas is perfluoropropane. The plurality of lipids can be a plurality of cationic lipids. For example, the plurality of lipids includes 1,2-dipalmitoyl-sn-glycero-3-phosphatidylcholine and 1,2-dipalmitoyl-sn-glycero-3-phosphatidyl ethanolamine.

Also disclosed here are methods of managing diabetes in a mammal. One such method includes the steps of providing a microbubble suspension containing a first non-viral nucleic acid construct with a first expression cassette encoding a positive regulatory domain zinc finger protein 16, a second non-viral nucleic acid construct with a second expression cassette encoding a peroxisome proliferator-activated receptor gamma coactivator 1-alpha protein, and a third non-viral nucleic acid construct with a third expression cassette encoding a bone morphogenetic protein 7. The steps further include introducing the microbubble suspension into a target cell of the mammal in vivo and exposing the target cell to ultrasound waves to release the first non-viral nucleic acid construct, the second nucleic acid construct, and the third nucleic acid construct. The first non-viral nucleic acid construct is expressed by the target cell to provide the positive regulatory domain zinc finger protein 16, the second nucleic acid construct is expressed by the target cell to provide the peroxisome proliferator-activated receptor gamma coactivator 1-alpha protein, and the third nucleic acid construct is expressed by the target cell to provide the bone morphogenetic protein 7 at levels sufficient to increase expression of mitochondrial uncoupling protein in the target cell. The target cell can be a skeletal muscle cell. In certain embodiments, the target cell is exposed to ultrasound waves applied in an ultraharmonic mode. In certain embodiments, the microbubble suspension is formed by mixing the first non-viral nucleic acid construct, the second non-viral nucleic acid construct, and a third non-viral nucleic acid construct with a plurality of lipids and a gas suitable for ultrasound-targeted microbubble destruction. In certain embodiments, the gas is perfluoropropane. The plurality of lipids can be a plurality of cationic lipids. For example, the plurality of lipids includes 1,2-dipalmitoyl-sn-glycero-3-phosphatidylcholine and 1,2-dipalmitoyl-sn-glycero-3-phosphatidyl ethanolamine.

Numerous other aspects, features and benefits of the present disclosure may be made apparent from the following detailed description taken together with the drawing figures. The pharmaceutical compositions can include nucleic acid constructs described herein along with other components, or ingredients depending on desired prevention and treatment goals. It should be further understood that both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawings will be provided by the U.S. Patent Office upon request and payment of the necessary fee. The present disclosure can be better understood by referring to the following figures.

FIG. 3A is an image showing the lack of expression of mUCP-1 gene in adult rat skeletal muscle after UTMD-mediated gene delivery of UTMD-DsRed/hyPB gene plasmids to the left thigh. FIG. 3B is an image showing the lack of expression of mUCP-1 gene in adult rat skeletal muscle after UTMD-mediated gene delivery of control plasmid to the right thigh. FIG. 3C is an image showing the mild expression of mUCP-1 gene in adult rat skeletal muscle after UTMD-mediated gene delivery of UTMD-pCMV-PRDM16 gene plasmids to left thigh. FIG. 3D is an image showing the lack of expression of mUCP-1 gene in adult rat skeletal muscle after UTMD-mediated gene delivery of control plasmid to the right thigh. FIG. 3E is an image showing moderate expression of mUCP-1 gene in adult rat skeletal muscle after UTMD-mediated gene delivery of UTMD-PRDM16/hyPB gene plasmids to the left thigh. FIG. 3F is an image showing the lack of expression of mUCP-1 gene in adult rat skeletal muscle after UTMD-mediated gene delivery of control plasmid to the right thigh. FIG. 3G is an image showing robust expression of mUCP-1 gene in adult rat skeletal muscle after UTMD-mediated gene delivery of UTMD-PRDM16/PGC-1α/BMP7/hyPB gene plasmids to the left thigh. FIG. 3H is an image showing the lack of expression of control plasmid on right thigh.

FIG. 3J is an image showing the lack of expression of PRDM16 gene in adult rat skeletal muscle after UTMD-mediated gene delivery of UTMD-DsRed/hyPB gene plasmids to the treated left thigh; and FIG. 3K is an image showing the lack of expression of PRDM16 gene in adult rat skeletal muscle after UTMD-mediated gene delivery of control plasmid to the right thigh. FIG. 3L is an image showing a mild expression of PRDM16 gene in adult rat skeletal muscle after UTMD-mediated gene delivery of UTMD-pCMV-PRDM16 gene plasmids to the left thigh; and FIG. 3M is an image showing the lack of expression of PRDM16 gene in adult rat skeletal muscle after UTMD-mediated gene delivery of control plasmid to the right thigh. FIG. 3N is an image showing moderate expression of PRDM16 gene in adult rat skeletal muscle after UTMD-mediated gene delivery of UTMD-PRDM16/hyPB gene plasmids on left thigh; and FIG. 3O is an image showing the lack of expression of PRDM16 gene in adult rat skeletal muscle after UTMD-mediated gene delivery of control plasmid to the right thigh. FIG. 3P is an image showing robust expression of PRDM16 gene in adult rat skeletal muscle after UTMD-mediated gene delivery of UTMD-PRDM16/PGC-1α/BMP7/hyPB plasmids to left thigh; and FIG. 3Q is an image showing the lack of expression of PRDM16 gene in adult rat skeletal muscle after UTMD-mediated gene delivery of control plasmid to the right thigh.

FIG. 4A is an image showing the lack of mUCP-1 expression in adult mice skeletal muscle after UTMD gene delivery of UTMD-DsRed/hyPB gene plasmids to the left thigh and FIG. 4B is an image showing the lack of expression of mUCP1 in adult mice skeletal muscle after UTMD-mediated gene delivery of control plasmids to the right thigh in wild type mice. FIG. 4C is an image showing robust expression of mUCP1 in adult mice skeletal muscle after UTMD-mediated gene delivery of UTMD-PRDM16/hyPB gene plasmids to the left thigh and FIG. 4D is an image showing the lack of expression of mUCP1 in adult mice skeletal muscle after UTMD-mediated gene delivery of control plasmid to the right thigh in wild type mice. FIG. 4E is an image showing lack of mUCP1 expression in adult mice skeletal muscle after UTMD-mediated gene delivery of UTMD-PRDM16/hyPB gene plasmids to the left thigh in mUCP-1 knock-out mice and FIG. 4F is an image showing the lack of expression of mUCP1 in adult mice skeletal muscle after UTMD-mediated gene delivery of control plasmid to right thigh in mUCP-1 knock-out mice.

FIG. 4H is an image showing the lack of PRMD16 expression after UTMD gene delivery of UTMD-DsRed/hyPB gene plasmids on left thigh and FIG. 4I is an image showing the lack of PRMD16 expression after UTMD gene delivery of control plasmid to the right thigh in wild type mice. FIG. 4J is an image showing the expression of PRMD16 in adult mice skeletal muscle after UTMD gene delivery of UTMD-PRDM16/hyPB gene plasmids to the left thigh of wild-type mice. FIG. 4K is an image showing lack of the expression of PRMD16 in adult mice skeletal muscle after UTMD gene delivery of control plasmids to the right thigh in wild type mice. FIG. 4L is an image showing the expression of PRMD16 in adult mice skeletal muscle after UTMD gene delivery of UTMD-PRDM16/hyPB gene plasmids to the left thigh of a mUCP-1 knock-out mouse and FIG. 4M is an image showing lack of the expression of PRMD16 in adult mice skeletal muscle after UTMD gene delivery of control plasmid to the right thigh of a mUCP-1 knock-out mouse.

FIG. 5A is an image showing lack of expression of Perilipin A after UTMD-mediated gene delivery of UTMD-DsRed/hyPB gene plasmids to the left thigh and FIG. 5B is an image showing lack of expression of Perilipin A after UTMD-mediated gene delivery of control plasmid to the right thigh in wild type mice. FIG. 5C is an image showing robust expression of Perilipin A in mice after UTMD-mediated gene delivery of UTMD-PRDM16/hyPB gene plasmids to the left thigh and FIG. 5D is an image showing lack of expression of Perilipin A after UTMD-mediated gene delivery of control plasmid on right thigh in wild type mice. FIG. 5E is an image showing lack of the expression of Perilipin A in mUCP-1 knock-out mice after UTMD-mediated gene delivery of UTMD-PRDM16/hyPB gene plasmids to the left thigh and FIG. 5F is an image showing lack of expression of Perilipin A after UTMD-mediated gene delivery of control plasmid to the right thigh of the mUCP-1 knock-out mice.

FIG. 5G is an image showing lack of co-localization of adipose marker, Perilipin A and the neutral lipid dye (oil red O) in wild type mice after UTMD-mediated gene delivery of UTMD-DsRed/hyPB gene plasmids to the left thigh and FIG. 5H is an image showing lack of co-localization of adipose marker, Perilipin A and the neutral lipid dye (oil red O) in wild type mice after UTMD-mediated gene delivery of control plasmid to the right thigh.

FIG. 5I is an image showing strong co-localization of adipose marker, Perilipin A and the neutral lipid dye (oil red O) in wild type mice after UTMD-mediated gene delivery of UTMD-PRDM16/hyPB gene plasmids to the left thigh and FIG. 5J is an image lacking co-localization of adipose marker, Perilipin A and the neutral lipid dye (oil red O) in wild type mice after UTMD-mediated gene delivery of control plasmid to the right thigh. FIG. 5K is an image lacking co-localization of adipose marker, Perilipin A and the neutral lipid dye (oil red O) in mUCP-1 knock-out mice after UTMD-mediated gene delivery of UTMD-PRDM16/hyPB gene plasmids to the left thigh and FIG. 5L is an image showing lack of co-localization of adipose marker, Perilipin A and the neutral lipid dye (oil red O) in mUCP-1 knock-out mice after UTMD-mediated gene delivery of control plasmid to the right thigh. FIG. 5M is a graphical representation of Perilipin A cDNA levels as measured by qRT-PCR for the samples captured in FIGS. 5A-5F. FIG. 5N is an image of a Western blot analysis detecting levels of expression of PRDM16, mUCP-1, and perilipin A proteins in skeletal muscle. FIGS. 5O-5R are magnified images of cell identified by a square in FIG. 5I.

FIGS. 6A (day 10) and 6C (day 20) show triple staining for muscle tissue in the left thigh at magnification of 200×, using anti-UCP-1 (red) and anti-Myf5 (green) antibodies in muscle tissues of rats treated with plasmid composition containing PRDM16, PGC-1a and BMP7 with a very strong UCP-1 signal. FIGS. 6B and 6D show a strong detection of Myf5+(green) and no UCP-1 signal detected in the right thigh of the control rats in muscle tissues of rats treated with control plasmids (magnification at 200×).

DETAILED DESCRIPTION

Figure 1A:
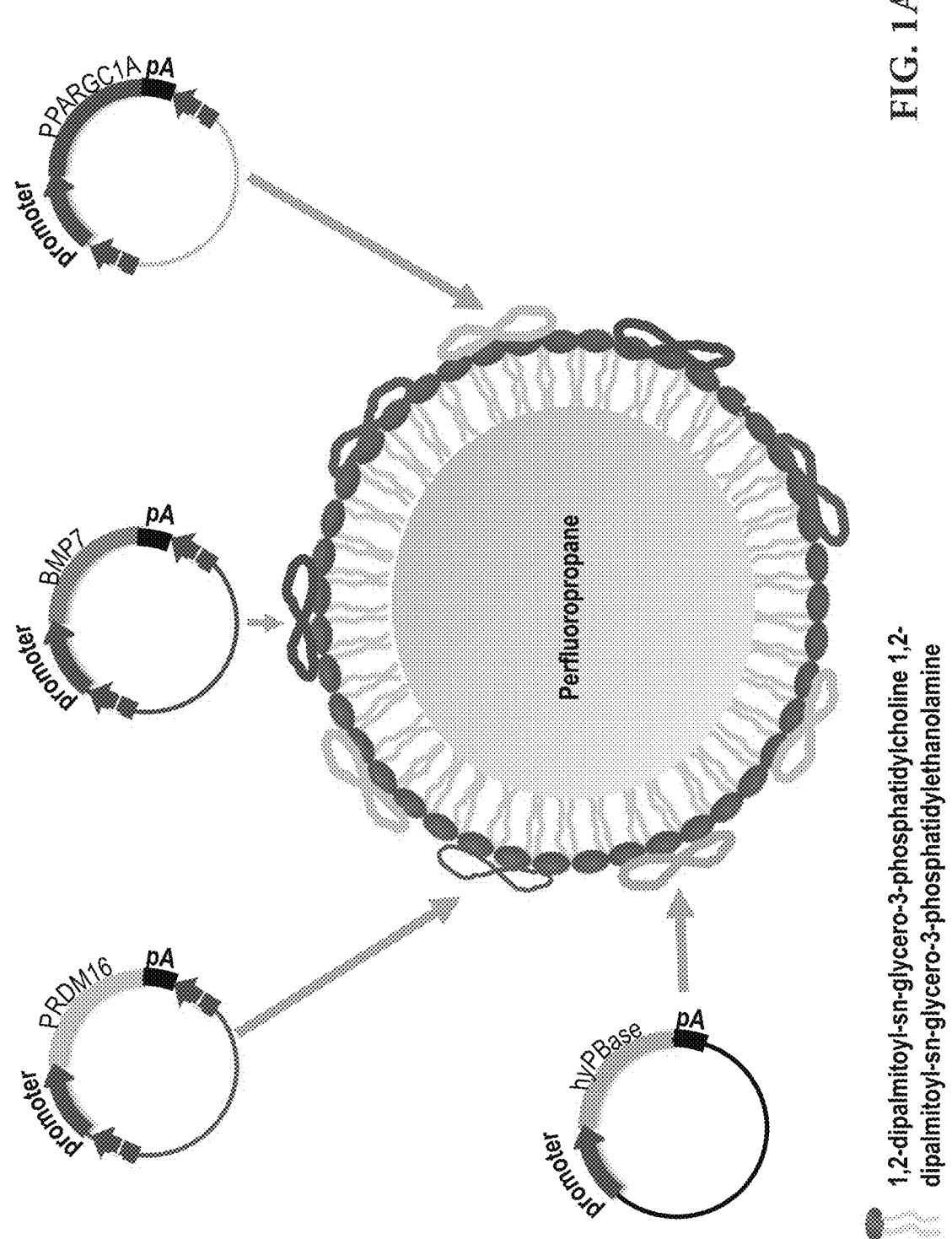
FIG. 1A is a diagrammatic representation of the nucleic acid constructs that are mixed with liposomes to form liposome-nucleic acid complexes, according to an embodiment.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

Disclosed here are compositions containing genes encoding PRDM16 (Positive Regulatory Domain Zinc Finger Protein 16), PGC-1α (or peroxisome proliferator-activated receptor gamma coactivator 1-alpha), and BMP7 (Bone morphogenetic protein 7). The publicly available sequences were used in these experiments.

PRDM16 is a 170 kilodalton member of the PR Domain family of proteins. It is a transcriptional regulator expressed in the embryo, and is reported to participate in the maintenance of both neuronal and hematopoietic progenitor stem cells populations, and to preferentially promote the development of brown fat from adipomyocyte precursors. Mouse PRDM16 is 1275 amino acids in length. It contains one SET domain followed by ten C2H2 type Zn finger motifs. Mouse PRDM16 shares 81% and 95% amino acid identity with human and rat PRDM16, respectively. For PRDM16, the human sequence is available at http://www.uniprot.org/uniprot/Q9HAZ2.

PGC-1α is a 97120 kDa member of the PGC1 family of proteins. It is expressed in select cell types, including brown adipocytes, skeletal muscle and hepatocytes. PGC-1α participates in both RNA processing and transcriptional coactivation in conjunction with multiple nuclear hormone receptors such as PPARy, RAR and TR. Human PCG1a is 798 amino acids in length. PGC-1α activity is regulated by phosphorylation. For PGC-1α, the human sequence is available at https://www.ncbi.nlm.nih.gov/gene/10891.

Adipogenesis is controlled by BMPs. BMP2 and BMP4 promote the development of white adipose tissue, whereas BMP7 promotes the development of skeletal muscles. BMP7, also known as osteogenic protein 1 (OP1), is a widely expressed TGFβ superfamily member. BMP7 also induces the expression of PRDM16 which functions to promote skeletal muscles gene expression and suppress the white fat program. Precursor cells, positive for the muscle developmental gene Myf5, are stimulated by BMP7 to express PRDM16, which acts as a switch to instigate the brown fat differentiation pathway and inhibit the white adipose tissue and myogenic pathway. PRDM16 acts to induce the expression of PGC-1α. Activation of PGC-1α by BMP7 and PRDM16 drives a complete brown fat differentiation program and UCP-1 expression. Mouse BMP7 is synthesized with a 29 amino acid (aa) signal sequence, a 262 aa propeptide, and a 139 aa growth factor domain. The growth factor domain of mouse BMP7 shares 98% and 100% aa sequence identity with human and rat BMP7, respectively. The BMP7 propeptide is cleaved intracellularly but remains in association with the growth factor domain. BMP7 is subsequently secreted as a tetramer that consists of two propeptides and two disulfide-linked growth factor domains. For BMP7, the human sequence is available at: http://www.uniprot.org/uniprot/P18075.

PRDM16 is a 170 kilodalton member of the PR Domain family of proteins. It is a transcriptional regulator expressed in the embryo, and is reported to participate in the maintenance of both neuronal and hematopoietic progenitor stem cells populations, and to preferentially promote the development of brown fat from adipomyocyte precursors. Mouse PRDM16 is 1275 amino acids in length. It contains one SET domain followed by ten C2H2 type Zn finger motifs. Mouse PRDM16 shares 81% and 95% amino acid identity with human and rat PRDM16, respectively. For PRDM16, the human sequence is available at www.uniprot.org/uniprot/Q9HAZ2.

PGC-1α is a 97120 kDa member of the PGC1 family of proteins. It is expressed in select cell types, including brown adipocytes, skeletal muscle and hepatocytes. PGC-1α participates in both RNA processing and transcriptional coactivation in conjunction with multiple nuclear hormone receptors such as PPARγ, RAR and TR. Human PCG1a is 798 amino acids in length. PGC-1α activity is regulated by phosphorylation. For PGC-1α, the human sequence is available at www.ncbi.nlm.nih.gov/gene/10891.

Adipogenesis is controlled by BMPs. BMP2 and BMP4 promote the development of white adipose tissue, whereas BMP7 promotes the development of skeletal muscles. BMP7, also known as osteogenic protein 1 (OP1), is a widely expressed TGFβ superfamily member. BMP7 also induces the expression of PRDM16 which functions to promote skeletal muscles gene expression and suppress the white fat program. Precursor cells, positive for the muscle developmental gene Myf5, are stimulated by BMP7 to express PRDM16, which acts as a switch to instigate the brown fat differentiation pathway and inhibit the white adipose tissue and myogenic pathway. PRDM16 acts to induce the expression of PGC-1α. Activation of PGC-1α by BMP7 and PRDM16 drives a complete brown fat differentiation program and UCP-1 expression. Mouse BMP7 is synthesized with a 29 amino acid (aa) signal sequence, a 262 aa propeptide, and a 139 aa growth factor domain. The growth factor domain of mouse BMP7 shares 98% and 100% aa sequence identity with human and rat BMP7, respectively. The BMP7 propeptide is cleaved intracellularly but remains in association with the growth factor domain. BMP7 is subsequently secreted as a tetramer that consists of two propeptides and two disulfide-linked growth factor domains. For BMP7, the human sequence is available at: www.uniprot.org/uniprot/P18075.

A nucleotide composition or a sequence "encoding" a polypeptide or a gene means a nucleotide sequence that, when transcribed and/or expressed, results in the production of an RNA, polypeptide or protein. The nucleotide sequence "encodes" that RNA or it encodes the amino acid sequence for that polypeptide or protein. The nucleic acid compositions may contain an element(s) that permits stable integration of the nucleic acid, or of a smaller part of the nucleic acid, into the host cell genome or autonomous replication of the nucleic acid composition independent of the genome of the cell.

The term "biologically functional equivalent" is well understood in the art and is further defined in detail herein. Accordingly, allowing for the degeneracy of the genetic code, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of nucleotides that are identical or functionally equivalent to the nucleotides of any of the sequences described herein will be biologically functional equivalents of the, provided the biological activity of the nucleotide sequence is maintained, for example, the publicly available sequences of PRDM16 at www.uniprot.org/uniprot/Q9HAZ2; PGC-1α at www.ncbi.nlm.nih.gov/gene/10891; and BMP7 at www.uniprot.org/uniprot/P18075.

In various embodiments, one or more nucleic acid constructs can be manufactured or delivered in the form of a pharmaceutical composition and may be used in the manufacture of a medicament or a pharmaceutical composition. The pharmaceutical compositions are suitable for administering effective amounts of the nucleic acid constructs disclosed here. The pharmaceutical composition can include a pharmaceutically acceptable carrier. For example, the pharmaceutical composition is formulated with a carrier that makes it suitable for intravenous administration. In other embodiments, the carrier can make the pharmaceutical composition suitable for parenteral or intramuscular administration. Examples of pharmaceutically acceptable carriers include one or more of sterile saline, dextrose solution, or buffered solution, or other pharmaceutically acceptable sterile fluids.

Metabolic diseases such as obesity are attractive candidates for gene therapy. The genes can be delivered using viral vectors delivery or non-viral delivery alternatives, such as ultrasound-targeted microbubble destruction (UTMD). UTMD is a method of tissue-specific gene delivery. This approach involves systemic infusion of transgenes precoupled to gas-filled lipid microbubbles. These microbubbles burst within the microvasculature of target tissues in response to an ultrasound signal. This results in release of DNA and transfection of neighboring cells within the tissue. Brown adipose tissue and skeletal muscles cells share common precursors, and brown adipose tissue is developmentally closer to skeletal muscles than to white adipose tissue.

Disclosed here are studies evaluating UTMD-mediated delivery of a cocktail of thermogenic brown adipose tissue genes (BMP7, PRDM16 and PGC-1α) to skeletal muscles to induce ectopic UCP-1 overexpression and thermogenesis. These studies revealed the advantages of the cocktail of thermogenic brown adipose tissue genes as compared to the delivery of PRDM16 alone; and also confirmed that the effects of the intervention are UCP-1-dependent.

In a study, ectopic mUCP-1 was overexpressed, which functions to dissipate energy as heat, in skeletal muscles of mice and rats that received thermogenic brown adipose tissue genes using nonviral, site-specific UTMD gene therapy.

"Brite", "beige", "inducible brown", or "recruitable brown" adipocytes exist among white adipocytes and upon stimulation by chronic cold exposure (or other mechanisms that mimic beta-adrenergic stimulation) they become multilocular and begin expressing UCP1. White adipose tissue browning is stimulated by a complex hormonal interplay and numerous environmental factors such as prolonged cold exposure, 0-adrenergic agonist treatment and exercise, and at the molecular level, it is regulated by multiple factors and signaling pathways. Peroxisome proliferator-activated receptor gamma coactivator 1-alpha (PGC-1α) functions as a master regulator of mitochondrial biogenesis and oxidative metabolism in adipocytes and inducing the expression of UCP1. Therefore, browning of white adipose tissue attracted attention as a potentially important, efficient strategy to treat obesity and its related metabolic disorders. However, white adipose tissue (WAT) has very few mitochondria and stores triglycerides as a single lipid droplet. On the other hand, brown adipose tissue has a large number of mitochondria in depots that are highly innervated and vascularized. Brown fat has a great capacity to oxidize fatty acids and generate heat, due to the presence of its unique gene coding for the mitochondrial uncoupling protein mUCP-1. Brown adipose tissue (BAT) has greater similarities to skeletal muscles than white adipose tissue. The developmental origins of brown adipose tissue and white adipose tissue are overall distinct, with brown adipocytes being derived from muscle precursors. White adipose cells originate from Myf5 negative (–) precursors and are derived from blood vessel-associated pericyte-like cells. Unlike white adipose tissue, a common lineage for skeletal muscles and brown fat cells has been proposed arising from the dermomyotome. BAT and skeletal muscle are derived from precursors expressing the key myogenic factor Myf5 positive.

From an evolutionary perspective, brown adipose tissue obtained the outstanding ability to develop thermogenic tissue of myogenic origin, to produce metabolic heat, to rapidly mobilize lipid droplets, and, similar to skeletal muscles, to possess large amounts of mitochondria. Skeletal muscles and brown adipose tissue seems to be complementary in their function. These organs appear to maintain a functional cross-talk and communicate with each other through myokines and adipokines during high metabolic demand including thermogenesis. Skeletal muscles is better vascularized compared to white adipose tissue. This was another important factor in choosing this tissue as the main target to deliver thermogenic brown adipose tissue genes with the UTMD technique. Skeletal muscles' mitochondrial uncoupling protein may drive endocrine cross-talk through the induction of myokine FGF21 released from skeletal muscles with endocrine effects. This leads to increased browning of white adipose tissue and can explain the healthy metabolic phenotype of UCP1-transgenic mice. PGC-1α is required for the expression of UCP1 in white adipose tissue and for the browning effect of FGF21.

Certain embodiments are described more fully hereinafter with reference to the accompanying drawings. These inventions may, however, be embodied in many different forms and should not be construed as limited to the exemplary embodiments set forth herein. Those skilled in the art will recognize that many changes and modifications may be made to the method of practicing the embodiments without departing the scope and spirit of the embodiments. Furthermore, language referring to order, such as first and second, should be understood in an exemplary sense and not in a limiting sense. For example, those skilled in the art may recognize that certain steps can be combined into a single step.

Disclosed here are nucleic acid compositions containing PRDM16, PGC-1α, and BMP7 expression cassettes. In an embodiment, a nucleic acid composition is a non-viral vector containing PRDM16, PGC-1α, and BMP7 expression cassettes. In certain embodiments, this nucleic acid composition was delivered to a skeletal muscle of an animal using ultrasound-targeted microbubble destruction. The nucleic acid compositions containing PRDM16, PGC-1α, and BMP7 expression cassettes are mixed with liposomes to form liposome-nucleic acid complexes. The liposome-nucleic acid complexes are suitable for in vivo ultrasound-targeted microbubble destruction. The liposome-nucleic acid complexes are present in a physiologically acceptable aqueous carrier, such as buffered water or saline. In an embodiment, the liposomes are lipid-coated or albumin coated microbubbles filled with a gas suitable for ultrasound microbubble destruction techniques, for example perfluoropropane. The liposome-nucleic acid complex may include cationic lipids, anionic lipids or mixtures and combinations thereof. The liposomes can also be multilamellar vesicles or unilamellar vesicles. Lipids for use in making the liposomes include 1,2-dipalmitoyl-sn-glycero-3-phosphatidylcholine or 1,2-dipalmitoyl-sn-glycero-3-phosphatidyl ethanolamine glycerol or cholesterol. The loaded microbubbles along in a pharmaceutically acceptable vehicle can be disposed in a liquid or dry form.

FIG. 1A is a diagrammatic representation of the nucleic acid constructs that are mixed with liposomes to form liposome-nucleic acid complexes, according to an embodiment. In an embodiment, the nucleic acid composition is a DNA transposon-based vector. This system includes the co-delivery of genetic material encoding the gene-inserting transposase protein-hyperactive piggyBac™ transposase protein (hyPB). In the embodiment shown in FIG. 1A, three plasmid cDNA constructs (PRDM16 cDNA, PGC-1α cDNA, BMP7 cDNA), were subcloned into piggyBac™ transposon pXL-BSII donor plasmids and hyperactive piggyBac™ transposase helper (hyPBase or hyPB) plasmids. In control studies, the DsRed cDNA construct was subcloned into piggyBac™ transposon pXL-BSII donor plasmids and hyPBase plasmids. Plasmid containing microbubbles were prepared with Lipofectamine®. Lipid-stabilized microbubbles were prepared containing 1,2-dipalmitoyl-sn-glycero-3-phosphatidylcholine and 1,2-dipalmitoyl-sn-glycero-3-phosphatidylethanolamine. The liposome/plasmid DNA mixture was added to glycerol and albumin solution to assemble a phospholipid-plasmid suspension. The air was replaced with perfluoropropane gas. In an embodiment, a cocktail of three thermogenic brown adipose tissue genes (PRDM16, BMP7, PGC-1α) were delivered into skeletal muscles. In another embodiment, a single PRMD16 was delivered into skeletal muscles. The triple cDNA construct was chosen to provide the complete set of genes in skeletal muscles that are key for the control and transcriptional regulation of classic brown fat cell differentiation and activation. BMP7 acts in an autocrine manner to induce brown committed (UCP1-neg) preadipocytes. BMP7 also induces the expression of PRDM16, which promotes the differentiation of mature brown adipocytes and suppresses both the white adipose tissue and the myogenic differentiation pathway. This leading to the expression of PGCla, that highly activates the expression of the final cellular product, the brown adipocyte specific gene mUCP-1. UCP-1 is the hallmark of brown adipose tissue, leading to metabolic heat production. As PRDM16 functions as the brown adipose tissue key regulator, the delivery of this gene was examined along with the triple construct.

The following nucleic acid compositions were evaluated in rat model:

UTMD delivery of pXL-BSII-CI-DsRed/hyPB plasmids;

UTMD delivery of pCMV-PRDM16 plasmid;

UTMD delivery of pXL-BSII-CI-PRDM16/hyPB plasmids; and

UTMD delivery of PRDM16/PGC-1α/BMP7/hyPB plasmids.

The following nucleic acid compositions were evaluated in wild-type mouse model:

UTMD delivery of pXL-BSII-DsRed/hyPB; and

UTMD delivery of pXL-BSII-CI-PRDM16/hyPB.

The following nucleic acid compositions were evaluated in mUCP-1$^{-/-}$ knock-out mouse model: UTMD delivery of pXL-BSII-CI-PRDM16/hyPB.

Phenotypic differences were examined, along with the effects on measurements for body weight, body weight changes, daily food intake, surface thigh temperature measured with infrared technology and abdominal subcutaneous fat thickness between triple compared to single gene delivery.

The changes in the food intake of the animals treated with the various nucleic acid compositions were measured. Rats were fed with access to 20 grams (g)/day and mice were fed with 3.5 g/day of a rodent high fat diet for one month before the UTMD mediated delivery of the nucleic acid compositions and then continued feeding with the same diet one month after UTMD procedures. The rats were eating~94 kilocalories per day (Kcal/day) and the mice~16.5 Kcal/day on the high fat diet (4.73 Kcal/g) before the gene therapy.

Figure 1B:
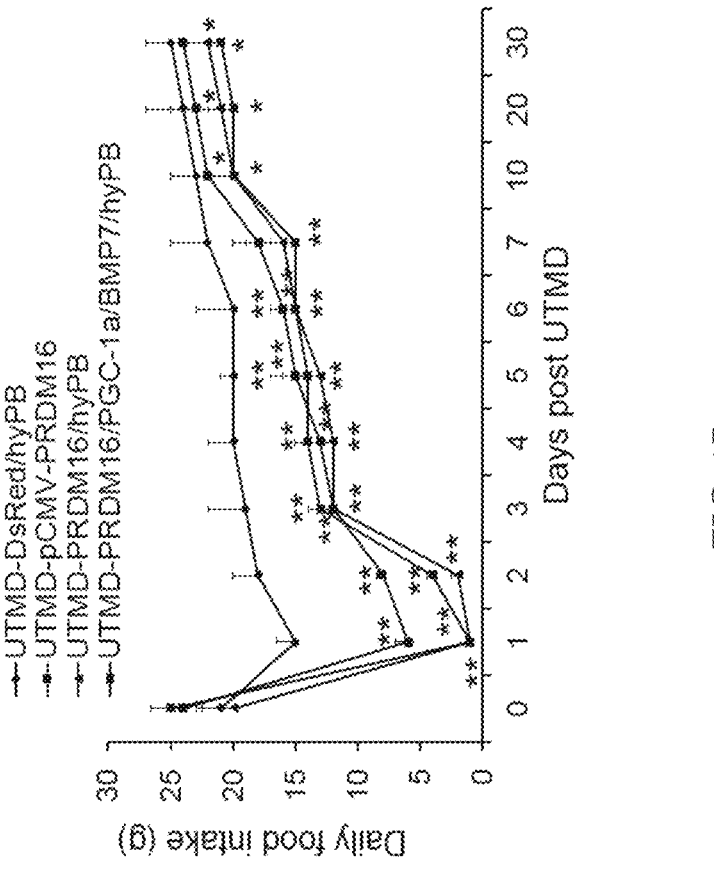
FIG. 1B is a graphical representation of the daily food intake (grams) in the rat model.

FIG. 1B is a graphical representation of the daily food intake (grams) in the rat model. Values are presented as mean±SEM (standard error of the mean), n=6 per group; * P<0.05, **P<0.001 vs DsRed control groups. FIG. 1B shows that food intake in rats sharply decreased in all animals within the first 3 days to 2-4 g (UTMD-PRDM16/hyPB or UTMD-PRDM16/PGC-1α/BMP7/hyPB), to 6-12 g (UTMD-pCMV-PRDM16), and to 16-18 g in the UTMD-DsRed/hyPB controls. Rats from all groups gradually increased their daily food intake between days 4 and 10, recovering the intake levels prior to UTMD gene therapy by day 20.

Figure 1C:
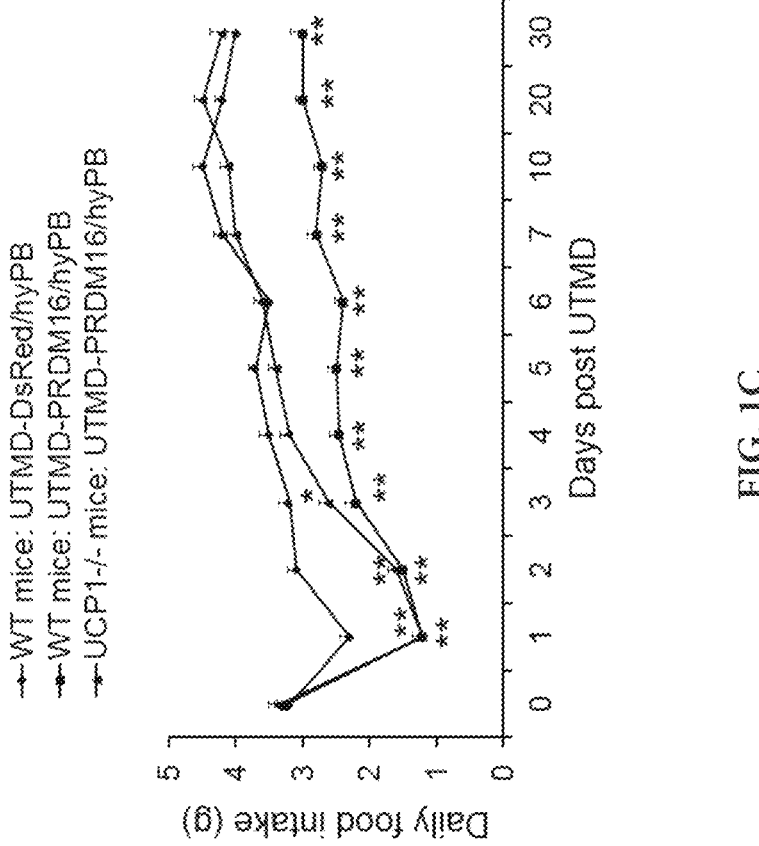
FIG. 1C is a graphical representation of daily food intake (grams) in the mice model.

FIG. 1C is a graphical representation of daily food intake (grams) in the mice model. Values are presented as mean±SEM, n=10 per group; * P<0.05, **P<0.001 vs control groups. FIG. 1C shows that mouse food intake also sharply decreased to 1 g after WT or UCP-1$^{-/-}$ knock-out mice received UTMD-PRDM16/hyPB. Both groups recovered their daily food intake between days 3 and 10, with a sharper increase in the UCP-1$^{-/-}$ knock-out mice. The group receiving UTMD-PRDM16/hyPB steadily kept their food intake after day 4 in 2.5 g range until day 30. WT mice receiving UTMD-DsRed/hyPB slightly decreased their food intake to 2.5 g and immediate recovered pre-UTMD administration levels.

The food intake results (FIGS. 1B and 1C) showed that the 30-day food intake pattern after gene therapy follows a tick mark-shape (✓), where the shape sharply falls within the first three days in the treated rats and WT or mUCP-1$^{-/-}$ knock-out mice receiving UTMD gene therapy with either the PRDM16/hyPB or the PRDM16/PGC-1α/BMP7/hyPB gene cocktail. Both rat and mice treated groups gradually increased their daily food intake, practically recovering the intake levels previous to gene therapy by day 30. This data shows that the gene therapy to rats with either the PRDM16/hyPB or the PRDM16/PGC-1α/BMP7/hyPB gene cocktail and wild type mice treated with UTMD-PRDM16/hyPB gene delivery consistently reduce daily food intake for short-term. This data indicates the association between the amounts of food consumption and UTMD-based gene administration in skeletal muscles.

Figure 1D:
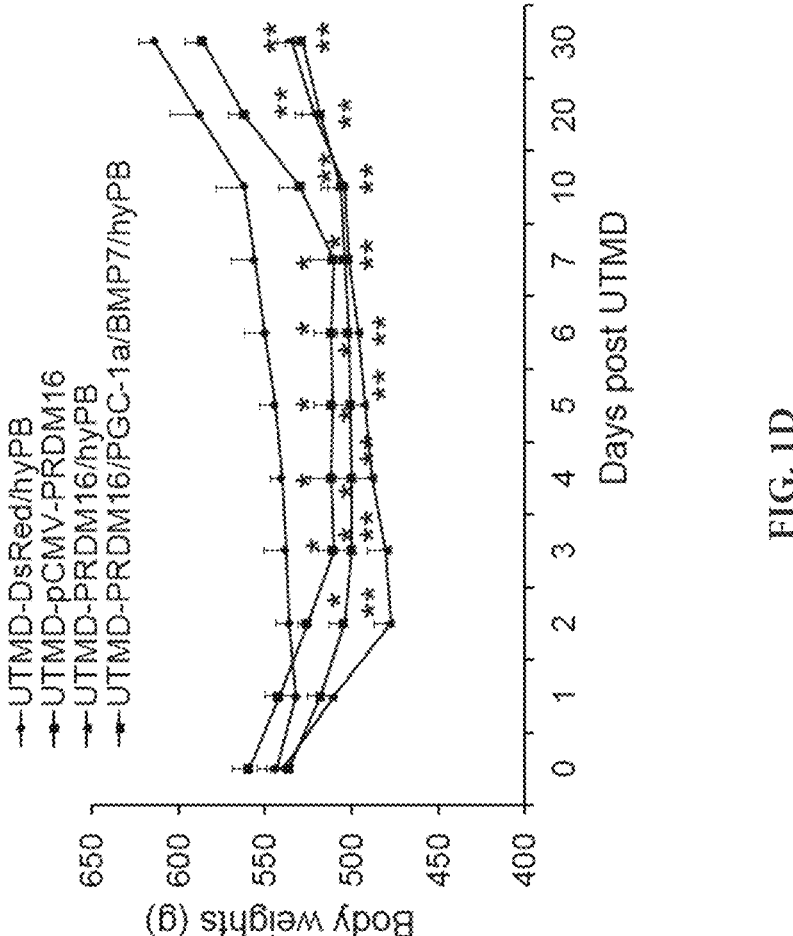
FIG. 1D is a graphical representation of rat body weights (grams).

The changes in the weight and fat loss of the animals treated with the various nucleic acid compositions were measured. FIG. 1D is a graphical representation of rat body weights (grams). Values are presented as mean±SEM, n=6 per group; * P<0.05, **P<0.001 vs DsRed control groups. In the rat model (FIG. 1D) body weights were not significantly different at baseline (~550 g, day 0). There was an interesting variation in their weight by day 30 after UTMD gene delivery, reaching 614±9, 586±10, 535±8, and 528±10 grams in the UTMD-DsRed/hyPB group, UTMD-pCMV-PRDM16 group (p<0.001 vs DsRed control group, n=6), UTMD-PRDM16/hyPB group (p<0.001 vs DsRed control group, n=6), and UTMD-PRDM16/PGC-1α/BMP7/hyPB group (p<0.001 vs DsRed control group, n=6) respectively.

Figure 1E:
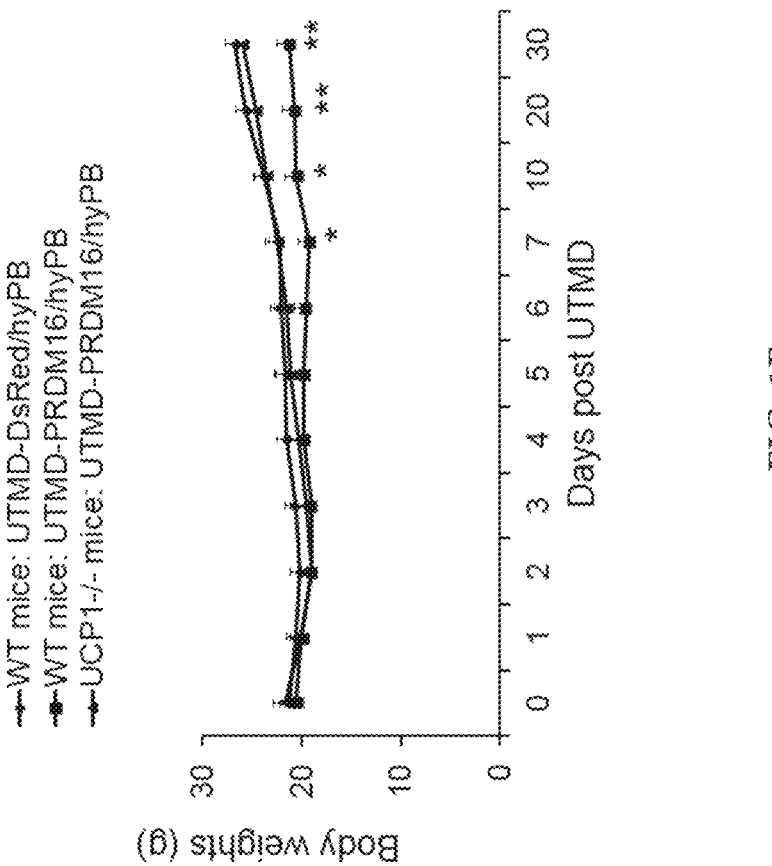
FIG. 1E is a graphical representation of mice body weights (grams).

FIG. 1E is a graphical representation of mice body weights (grams). Values are presented as mean±SEM, n=10 per group; * P<0.05, **P<0.001 vs control groups. FIGS. 1D and 1E show that the rats and mice started the treatment with UTMD gene therapy weighing~550 grams and ~22 grams, respectively. The rat group intervened with the PRDM16/hyPB or the PRDM16/PGC-1α/BMP7/hyPB gene cocktail ended up weighing~500 g compared to the rats receiving pCMV-PRDM16 or UTMD-DsRed/hyPB which ended up with a final weight higher to the one previous to the UTMD treatment (~600 g).

Figure 2A:
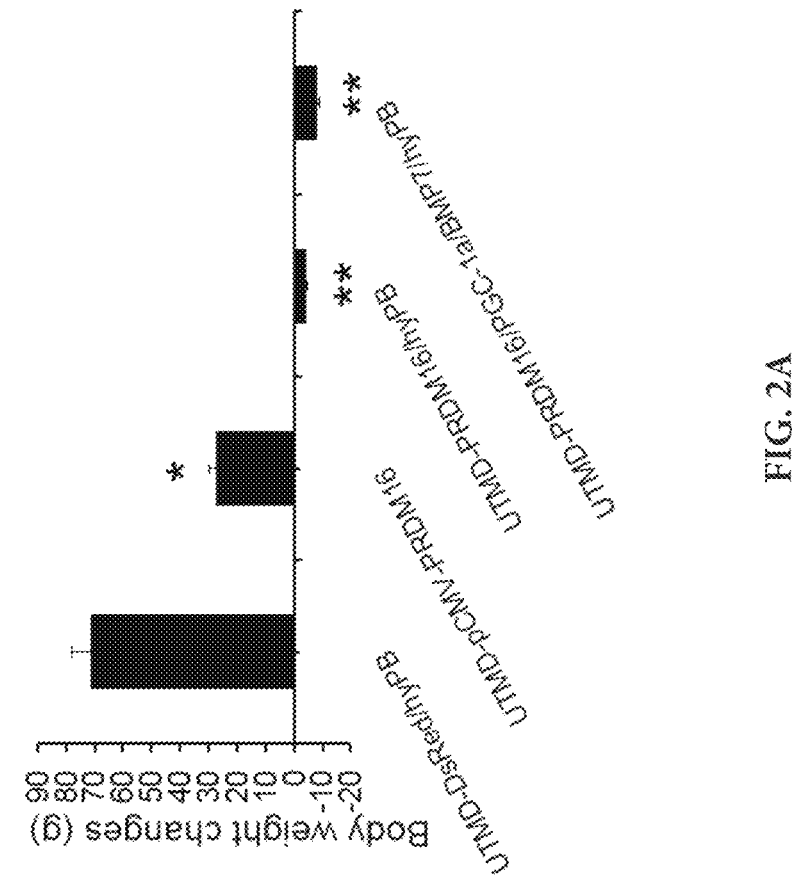
FIG. 2A is a graphical representation of rat body weight changes (grams).
Figure 2B:
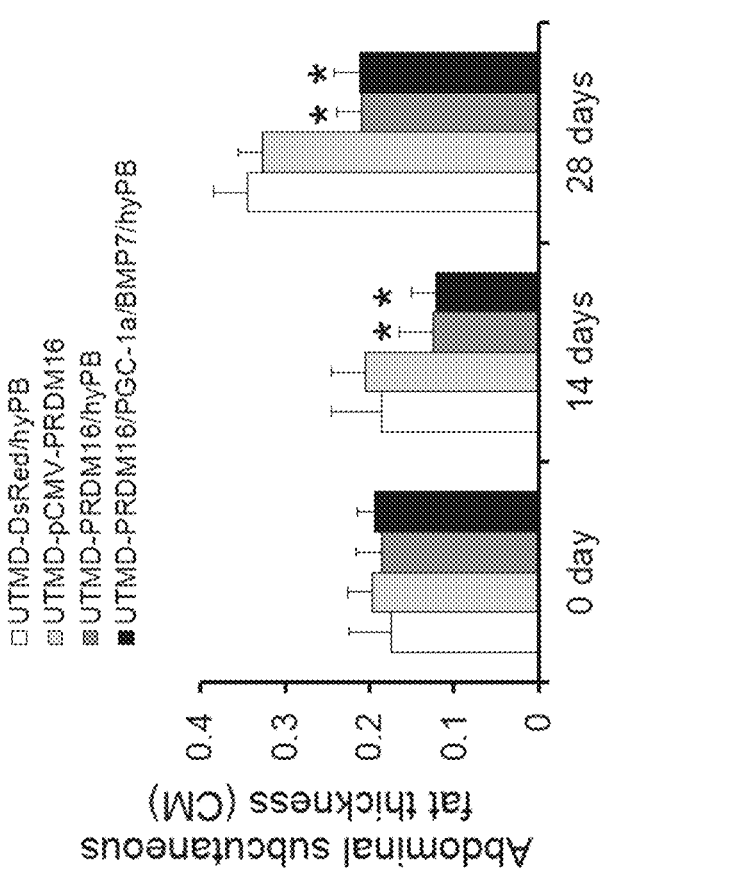
FIG. 2B is a graphical representation of the thickness of the abdominal subcutaneous fat layer.

The subcutaneous fat loss was evaluated by measuring the fat thickness using ultrasound images. The rat weight change and subcutaneous fat loss from the hyPB treated rats also resulted in a far greater percentage from fat mass compared to pCMV rats or hyPB/DsRed controls (FIGS. 2A and 2B). FIG. 2A is a graphical representation of rat body weight changes (grams). Values are presented as mean±SEM, n=6 per group; **P<0.001 vs DsRed control groups. FIG. 2A shows noticeable body weight loss in the UTMD-PRDM16/hyPB mice group and UTMD-PRDM16/PGC-1α/BMP7/hyPB group when compared to the UTMD-DsRed/hyPB or UTMD-pCMV-PRDM16 groups. Subcutaneous abdominal fat thickness (FIG. 2B) was measured with ultrasound (US) imaging in the rat model. The results show reduction in fat thickness in the PRDM16 gene administration or the gene cocktail delivery groups when compared to DsRed or pCMV-PRDM16 groups (P<0.05). FIG. 2B is a graphical representation of the thickness of the abdominal subcutaneous fat layer, Values are presented as mean±SEM, n=6 per group; * P<0.05 vs control groups. In the mice model (FIG. 1E), their body weights were practically similar at baseline (~22 g, day 0). One month post UTMD treatment their weights were 26.7±1.3, 21.2±1.2, and 25.9±1.4 g: UTMD-DsRed/hyPB group, WT mice: UTMD-PRDM16/hyPB group (p<0.001 vs DsRed control group, n=10), and UCP-1$^{-/-}$ knock-out mice: UTMD-PRDM16/hyPB group (p>0.05 vs DsRed control group, n=10) (FIG. 1E).

Brown adipose tissue thermogenesis was measured using infrared imaging following UTMD gene therapy. Temperature changes in both rodent models, using an infrared digital thermographic camera. The temperature increased in the targeted local left thigh area when compared with the right thigh control at 14 days or 28 days post UTMD gene delivery (P<0.05 vs control thighs or DsRed group) (FIG.

Figure 2C:
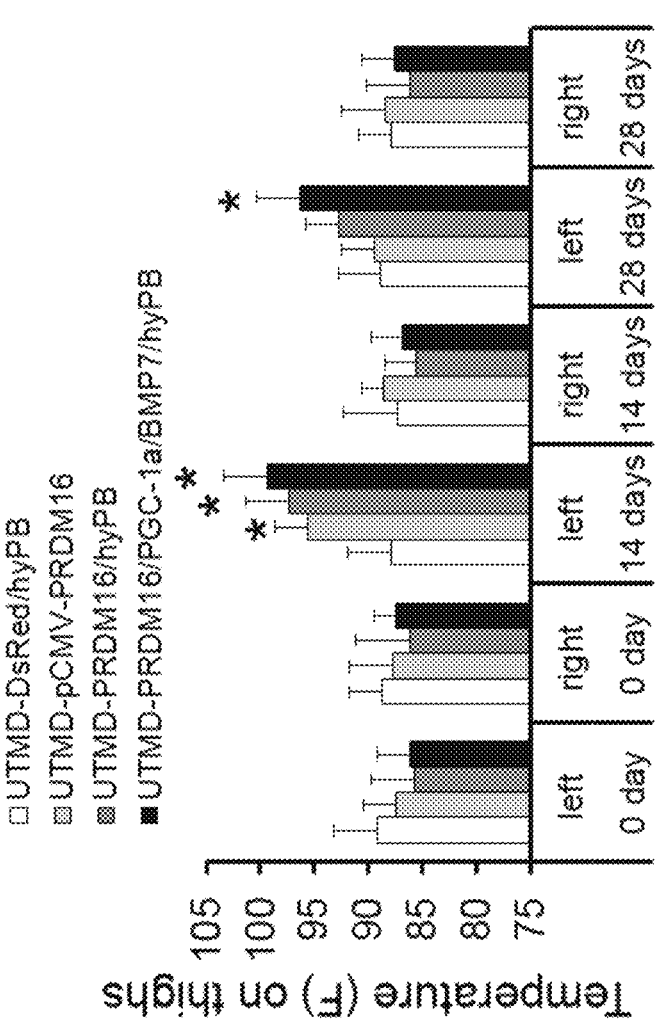
FIG. 2C is a graphical representation of temperature, as measured on the Fahrenheit scale, (F) on rat thighs.
Figure 2D:
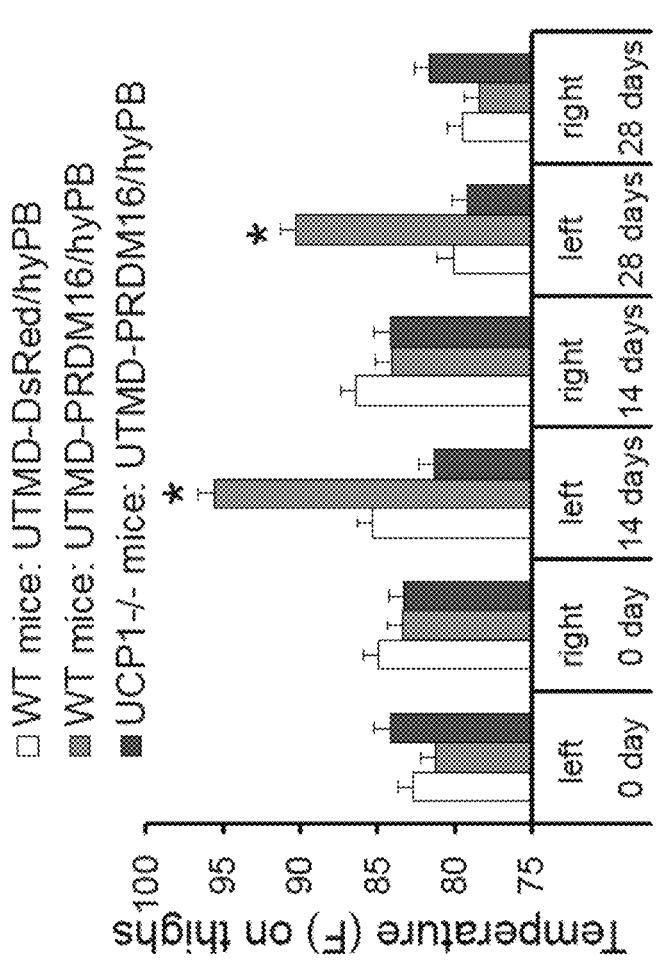
FIG. 2D is a graphical representation of temperature (F) on mice thighs.

2C and FIG. 2D). FIG. 2C is a graphical representation of temperature (F) on rat thighs. Values are presented as mean±SEM, n=6 per group; * P<0.05 vs control groups. FIG. 2D is a graphical representation of temperature (F) on mice thighs, Values are presented as mean±SEM, n=10 per group; * P<0.05 vs control groups. FIGS. 2C and 2D clearly show that in both rat and mice models there were an increase in body surface temperature observed using this method in the treated animals. The WT or mUCP-1$^{-/-}$ knock-out mice receiving the PRDM16/hyPB or UTMD-DsRed/hyPB increased their body weight at the end of 30 days (~27 g), also showing that the WT group receiving the PRDM16/hyPB maintained a quasi-flat line without any significant increase or decrease weight for 30 days. The highest temperature elevation seems to have been achieved in rats with the administration of the UTMD-PRDM16/PGC-1α/BMP7/hyPB gene cocktail (FIG. 2C, black bar). These results indicate that the significant increased temperature was due to mUCP-1-mediated thermogenesis. These findings represent the first standardized use of infrared imaging to specifically detect mUCP-1 activity after UTMD gene therapy, indicating that infrared thermography specifically detects mUCP-1-mediated thermogenesis in vivo and metabolic heat production in skeletal muscles.

It is important to obtain higher UCP1 overexpression levels, which would produce powerful clinically-translated thermogenic effects and metabolic heat production on food intake and energy expenditure. With the triple gene delivery, an energy gap was created and that explained why the rats gradually recovered their food intake patterns by day 30, when compared to the patterns they showed before gene therapy administration and to the food intake of their controls. The weight loss in the treated rats never recovered the levels observed in the controls in spite of food intake recovery (FIG. 1). In other words, the curve of food intake and weight loss in the treated rats and mice showed that these animals gradually recovered their food intake patterns by day 20, when compared with the patterns they showed before UTMD gene therapy administration and to the food intake of their controls. However, the weight loss in the treated rats and mice never recovered the levels observed in the controls despite food intake recovery. This finding may be associated with the new "energy gap" concept. Under the concept of an energy gap of ~50 g weight loss in 30 days, the treated rats did not regain their initial weight practically without a significant change in energy intake as Kcal/day. An overwhelming energy gap was not observed in the mice in this study experiencing single PRMD gene delivery as was observed in the rat model. Energy expenditure represented by thermogenesis is likely to explain the weight loss maintained in these rats regardless of food intake gradual recuperation, clearly indicating brown adipose tissue mUCP1 over activity and metabolic heat production secondary to UTMD gene therapy in skeletal muscles. This finding follows the efficacy of long-term weight loss achieved by bariatric surgery and its effectiveness to stimulate daily energy expenditure as the energy gap for long-term maintenance with apparent scanty changes in daily energy intake. This "energy gap" concept has been observed in the Swedish Obesity Subjects (SOS) trial showing that the efficacy of bariatric surgery to long-term weight loss is about 20 kg on average over 10-15 years. An analysis of the fall in energy expenditure (EE) for long-term weight loss achieved by bariatric surgery seems to have been effective in stimulating daily EE by approximately 600 kcal daily (considered the energy gap for long-term maintenance, and subdivided into components that represent passive (obligatory) and active (adaptive thermogenesis) components), assuming no change in energy intake. Given that an increase in 24-h EE documented from any thermogenic compound at a safe dose is less than 150 kcal/day, a valid question would be whether the human body is able to reach a thermogenic capacity from BAT to achieve similar long-term weight loss as the one obtained in the SOS trial. The precise interpretation of the higher gene expression of UCP-1 protein shown in FIGS. 3G and I, the temperature elevation in FIG. 2C, and the energy gap concept, support that short-term UTMD-based triple gene delivery is more effective than single PRMD16 gene delivery. Obese patients have a tendency to regain the weight that they lose. If, in response to weight loss, one can steadily stimulate the classical brown adipose tissue machinery and browning of white adipose tissue, it would help weight loss maintenance.

In vitro immunostaining or immunohistochemistry (IHC) for cell markers is an indirect method of gene amplification allowing identification of the histological origin of the cell indicating its function in vivo when the correct antibody is used. Positive and intense mUCP-1 and PRMD16 overexpression was detected through IHC, and significantly higher expression levels of these genes were measured by qRT-PCR, accurately localized in skeletal muscles surrounding the site of the thigh exposed to ultrasound implementation in the treated rats and mice as shown in FIGS. 3 and 4 after UTMD administration with either triple delivery or single gene therapy. These molecular observations nicely correlated with measurements by thermal infrared imaging showing a significant increase in surface temperature in the same skeletal muscles site (FIGS. 2C and 2D).

Figures 3A, 3B, 3C, 3D:
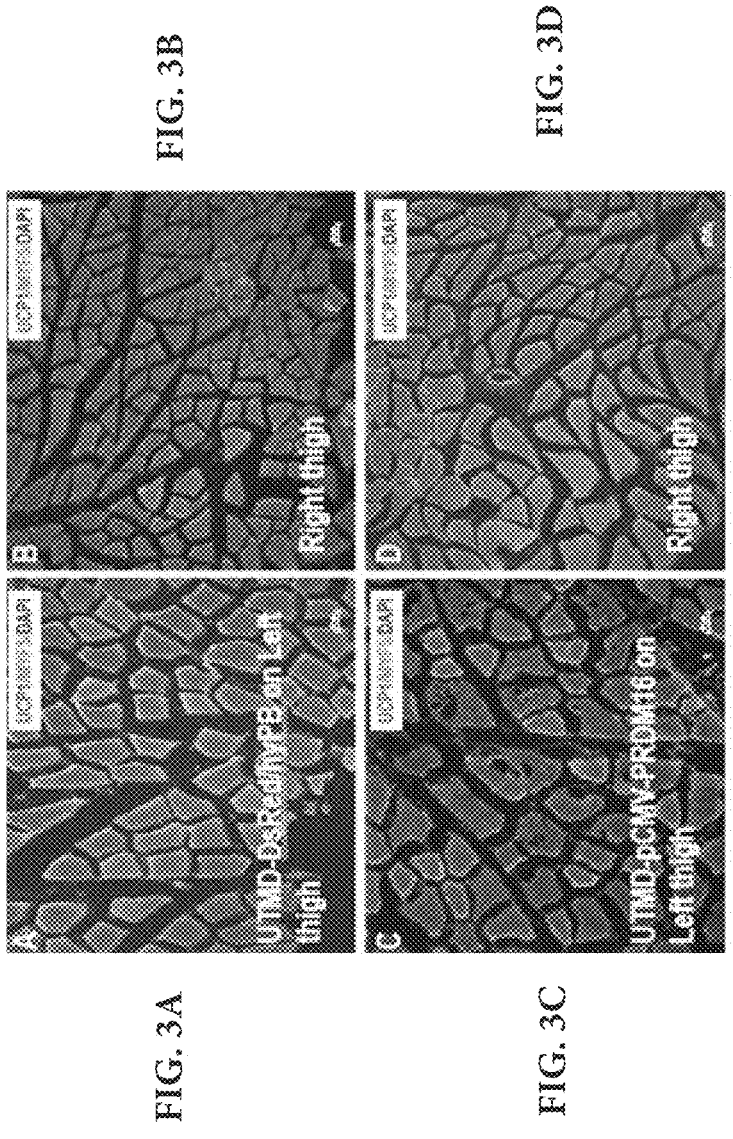
FIGS. 3A-3H are images showing the expression of mUCP-1 gene in adult rat skeletal muscle after UTMD-mediated gene delivery of different nucleic acid constructs.
Figures 3E, 3F, 3G, 3H:
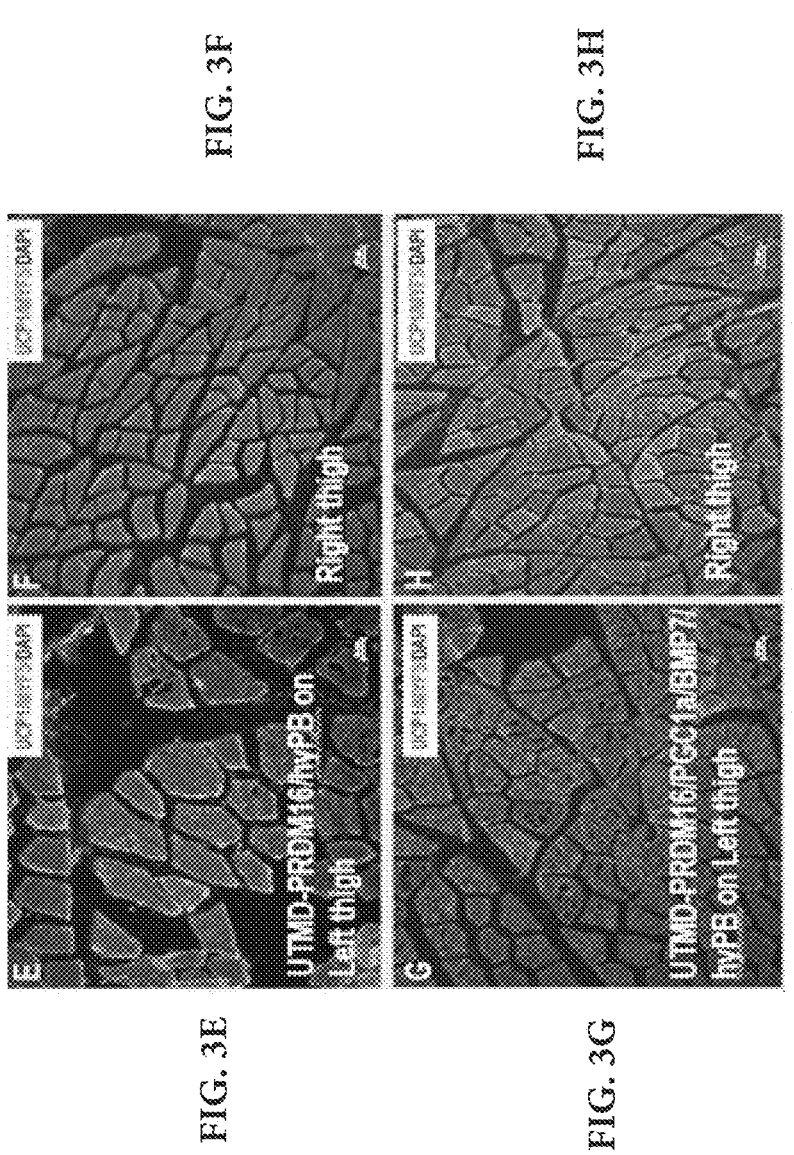

FIGS. 3A-3H is a series of images showing the expression of mUCP-1 gene in adult rat skeletal muscle after UTMD-mediated gene delivery of different nucleic acid constructs (anti-UCP-1 (red) and anti-Myf5 (green) antibodies for IHC). FIG. 3A is an image showing the lack of expression of mUCP-1 gene in adult rat skeletal muscle after UTMD-mediated gene delivery of UTMD-DsRed/hyPB gene plasmids to the left thigh. FIG. 3B is an image showing the lack of expression of mUCP-1 gene in adult rat skeletal muscle after UTMD-mediated gene delivery of control plasmid to the right thigh. FIG. 3C is an image showing a very weak expression of mUCP-1 gene in adult rat skeletal muscle after UTMD-mediated gene delivery of UTMD-pCMV-PRDM16 gene plasmids to left thigh. FIG. 3D is an image showing the lack of expression of mUCP-1 gene in adult rat skeletal muscle after UTMD-mediated gene delivery of control plasmid to the right thigh. FIG. 3E is an image showing a mild expression of mUCP-1 gene in adult rat skeletal muscle after UTMD-mediated gene delivery of UTMD-PRDM16/hyPB gene plasmids to the left thigh. FIG. 3F is an image showing the lack of expression of mUCP-1 gene in adult rat skeletal muscle after UTMD-mediated gene delivery of control plasmid to the right thigh. FIG. 3G is an image showing a very strong expression of mUCP-1 gene in adult rat skeletal muscle after UTMD-mediated gene delivery of UTMD-PRDM16/PGC-1α/BMP7/hyPB gene plasmids to the left thigh. FIG. 3H is an image showing the lack of expression of control plasmid on right thigh. Immunohistochemistry (IHC) from FIG. 3 shows that a remarkable mUCP-1 signal was detected in rat skeletal muscles cells one month after UTMD-pXL-BASII-CI-PRDM16/BMP7/PGC-1α gene cocktail was delivered to the site-specific left thighs (FIG. 3G), also detected in lesser intensity in the UTMD-pXL-BASII-CI-PRDM16/hyPB (FIG. 3E), but it was not seen in the right thigh controls (FIGS. 3F-H) nor in the controls treated with the UTMD-DsRed reporter gene (FIGS. 3A-B). mUCP-1 signal was significantly decreased in the regular CMV promoter driving the PRDM16 plasmid group (FIG. 3C).

Figure 3I:
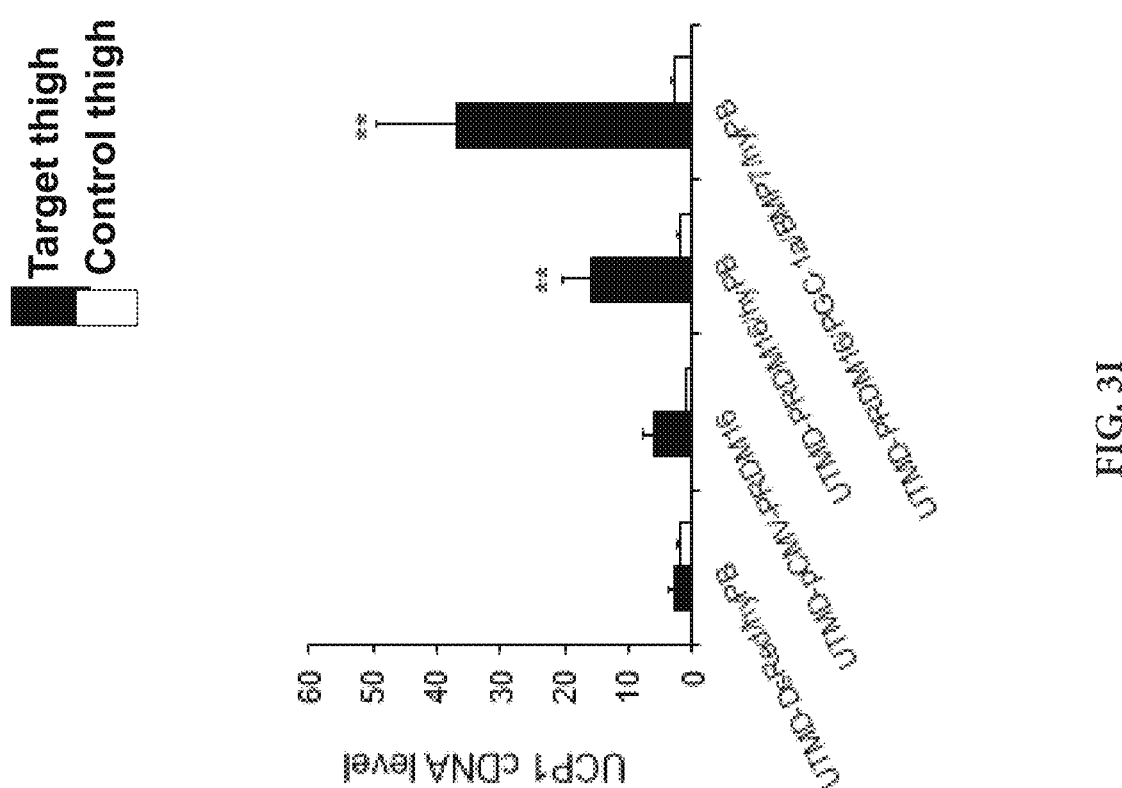
FIG. 3I is a graphical representation of mUCP-1 cDNA levels as measured by quantitative real-time reverse transcription polymerase chain reaction (qRT-PCR) for the samples captured in FIGS. 3A-3H.

FIG. 3I is a graphical representation of mUCP-1 cDNA levels as measured by quantitative real-time reverse transcription polymerase chain reaction (qRT-PCR) for the samples captured in FIGS. 3A-3H. Values are presented as mean±SEM. n=6 per group; * P<0.05, P<0.001 vs control thighs or DsRed group. The results of the mUCP-1 qRT-PCR gene expression (FIG. 3**I) shows that mUCP-1 cDNA levels in the treated left thigh after UTMD-pXL-BASII-CI-PRDM16/BMP7/PGC-1α gene cocktail were 36±9-fold greater than UTMD-pXL-BASII-CI-PRDM16/hyPB alone (18±3-fold (p<0.001).

Figures 3J, 3K, 3L, 3M:
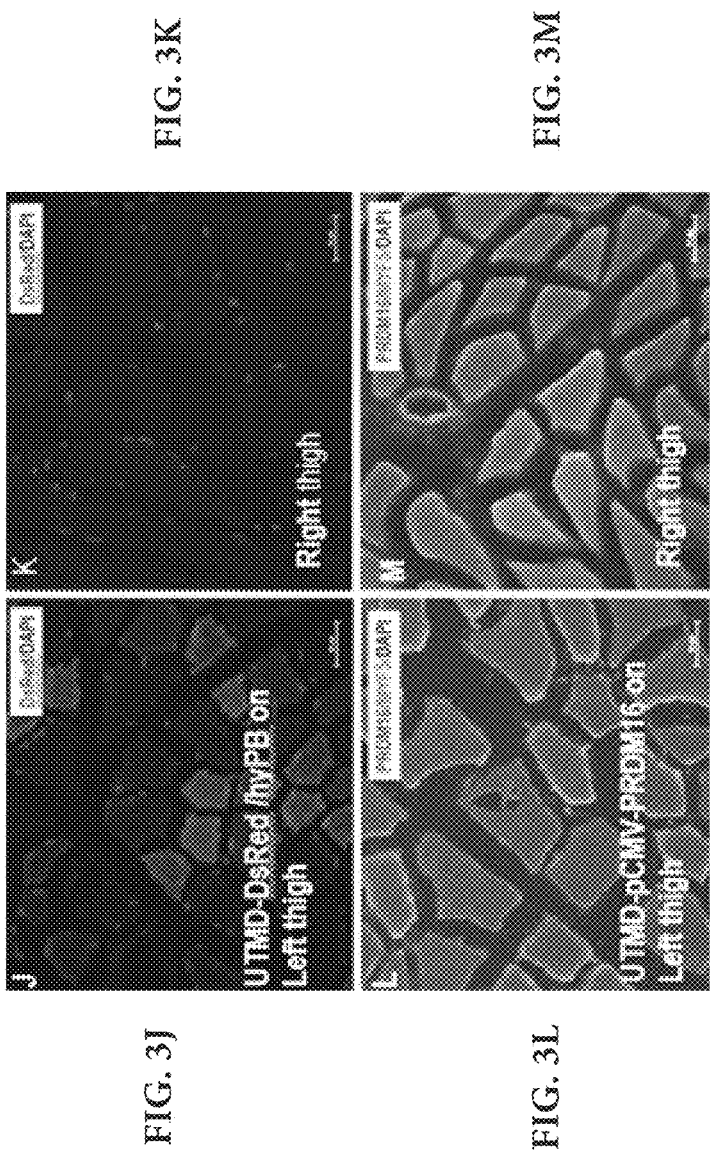
FIGS. 3J-3Q are images showing the expression of PRDM16 gene in adult rat skeletal muscle after UTMD-mediated gene delivery of different nucleic acid constructs.

The PRMD16 signal in rat skeletal muscles after UTMD gene delivery of different nucleic acid compositions was measured. The PRDM16 IHC and expression were measured with both CMV-promoter-driven plasmids and hyPB transposon plasmids in the UTMD gene delivery system. IHC from FIG. 3 also shows that a significant rat PRDM16 signal was detected in skeletal muscles cells one month after UTMD-pXL-BASII-CI-PRDM16/hyPB or PRDM16/BMP7/PGC-1α gene cocktail delivered to the left thighs (FIGS. 3N-P) but was not detected in the right thigh controls (FIGS. 3O-Q), nor in the controls treated with UTMD-DsRed reporter gene (FIGS. 3J-K). Moreover, PRDM16 signal was very weak in the regular CMV promoter driving the PRDM16 plasmid group (FIG. 3L). PRMD16 qRT-PCR gene expression showed a level of 76±4-fold and 82±8-fold after UTMD-pXL-BASII-CI-PRDM16/BMP7/PGC-1α gene cocktail and UTMD-pXL-BASII-CI-PRDM16/hyPB, respectively (p<0.001) (FIG. 3R).

Figures 3N, 3O, 3P, 3Q:
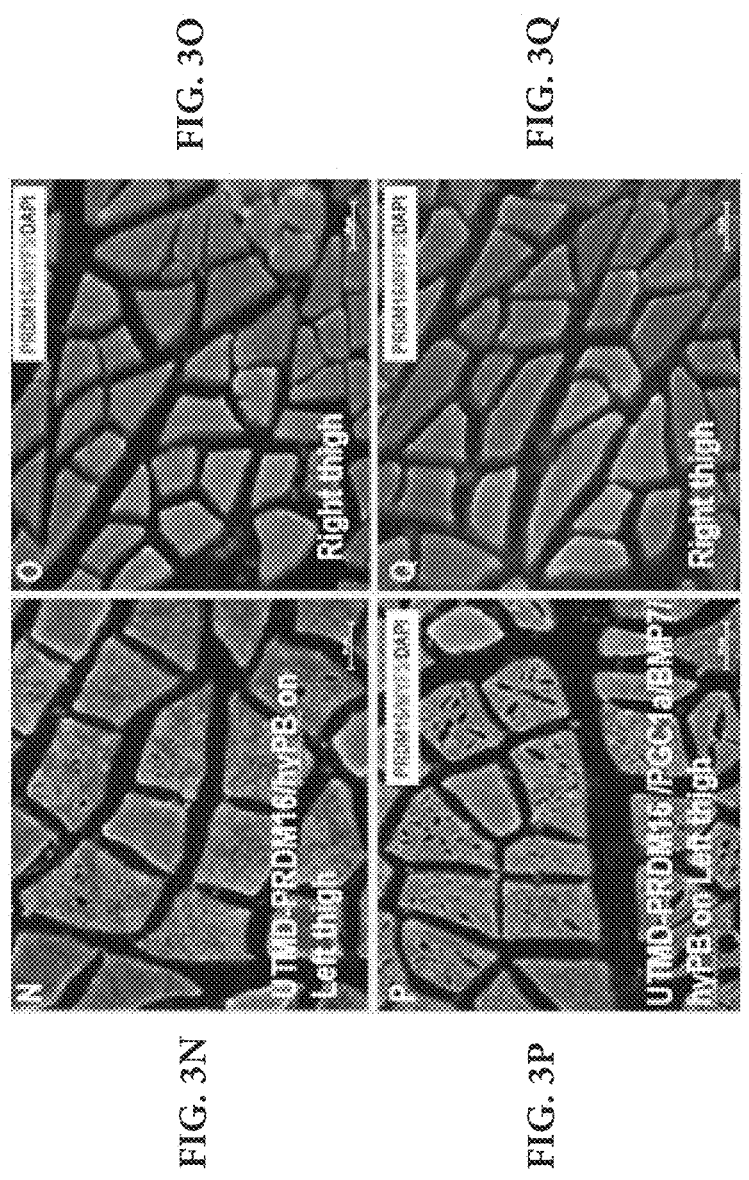

FIGS. 3J-3Q are images showing the expression of PRDM16 gene in adult rat skeletal muscle after UTMD-mediated gene delivery of different nucleic acid constructs. FIG. 3J is an image showing the lack of expression of PRDM16 gene in adult rat skeletal muscle after UTMD-mediated gene delivery of UTMD-DsRed/hyPB gene plasmids to the treated left thigh; and FIG. 3K is an image showing the lack of expression of PRDM16 gene in adult rat skeletal muscle after UTMD-mediated gene delivery of control plasmid to the right thigh. FIG. 3L is an image showing weak expression of PRDM16 gene in adult rat skeletal muscle after UTMD-mediated gene delivery of UTMD-pCMV-PRDM16 gene plasmids to the left thigh; and FIG. 3M is an image showing the lack of expression of PRDM16 gene in adult rat skeletal muscle after UTMD-mediated gene delivery of control plasmid to the right thigh. FIG. 3N is an image showing the expression of PRDM16 gene in adult rat skeletal muscle after UTMD-mediated gene delivery of UTMD-PRDM16/hyPB gene plasmids on left thigh; and FIG. 3O is an image showing the lack of expression of PRDM16 gene in adult rat skeletal muscle after UTMD-mediated gene delivery of control plasmid to the right thigh. FIG. 3P is an image showing strong expression of PRDM16 gene in adult rat skeletal muscle after UTMD-mediated gene delivery of UTMD-PRDM16/PGC-1α/BMP7/hyPB plasmids to left thigh; and FIG. 3Q is an image showing the lack of expression of PRDM16 gene in adult rat skeletal muscle after UTMD-mediated gene delivery of control plasmid to the right thigh. Scale bar is 50 μm.

Figure 3R:
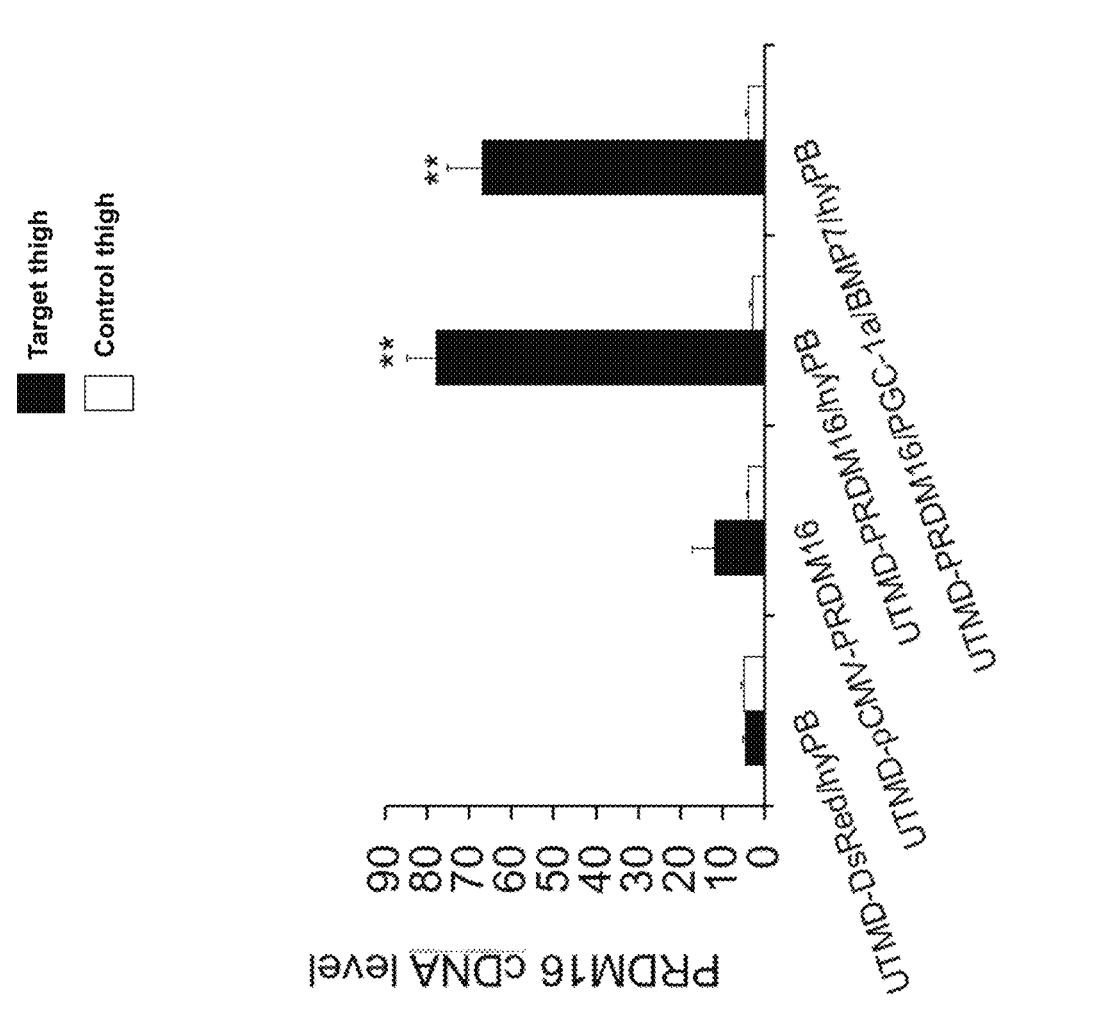
FIG. 3R is a graphical representation of PRDM16 cDNA levels as measured by quantitative real-time reverse transcription polymerase chain reaction (qRT-PCR) for the samples captured in FIGS. 3J-3Q.

FIG. 3R is a graphical representation of PRDM16 cDNA levels as measured by quantitative real-time reverse transcription polymerase chain reaction (qRT-PCR) for the samples captured in FIGS. 3J-3Q. Values are presented as mean±SEM, n=6 per group; * P<0.05, P<0.001 vs control thigh or DsRed group. UTMD-PRDM16/hyPB administration showed an 80-fold increased vs 5-fold increase (control site) of PRDM16 cDNA levels. UTMD-PRDM16/PGC-1α/BMP7/hyPB administration showed an 80-fold increased vs 5-fold increase (control site) of PRDM16 cDNA levels. Overall, the IHC data from the treated left thigh of the rat model (FIG. 3) show qualitative positive results for the presence of mUCP-1 and PRMD16, compared to the negative staining from skeletal muscles of the right thigh. Particularly, FIGS. 3G and 3**P strikingly show robust cellular presence of mUCP-1 and PRDM16 immunoexpression in the treated thigh after delivering the UTMD-PRDM16/PGC-1α/BMP7/hyPB gene cocktail.

These IHC data were reinforced and corroborated by quantitative RT-PCR analysis measuring rat PRDM16 and mUCP-1 cDNA levels. RT-PCR-based analysis of DNA offer a precise quantitative analysis of gene amplification, adding sensitivity and specificity to the IHC. Following the results of the rat IHC data from FIG. 3, rat mUCP-1 and PRDM16 cDNA levels were significantly higher (p<0.001) in the treated thigh after gene expression with piggyBac™ transposon plasmids in the UTMD gene delivery system when compared with the gene expression with regular CMV or the controls treated with UTMD-DsRed reporter gene (FIGS. 3I and 3R).

Figures 4A, 4B, 4C, 4D, 4E, 4F:
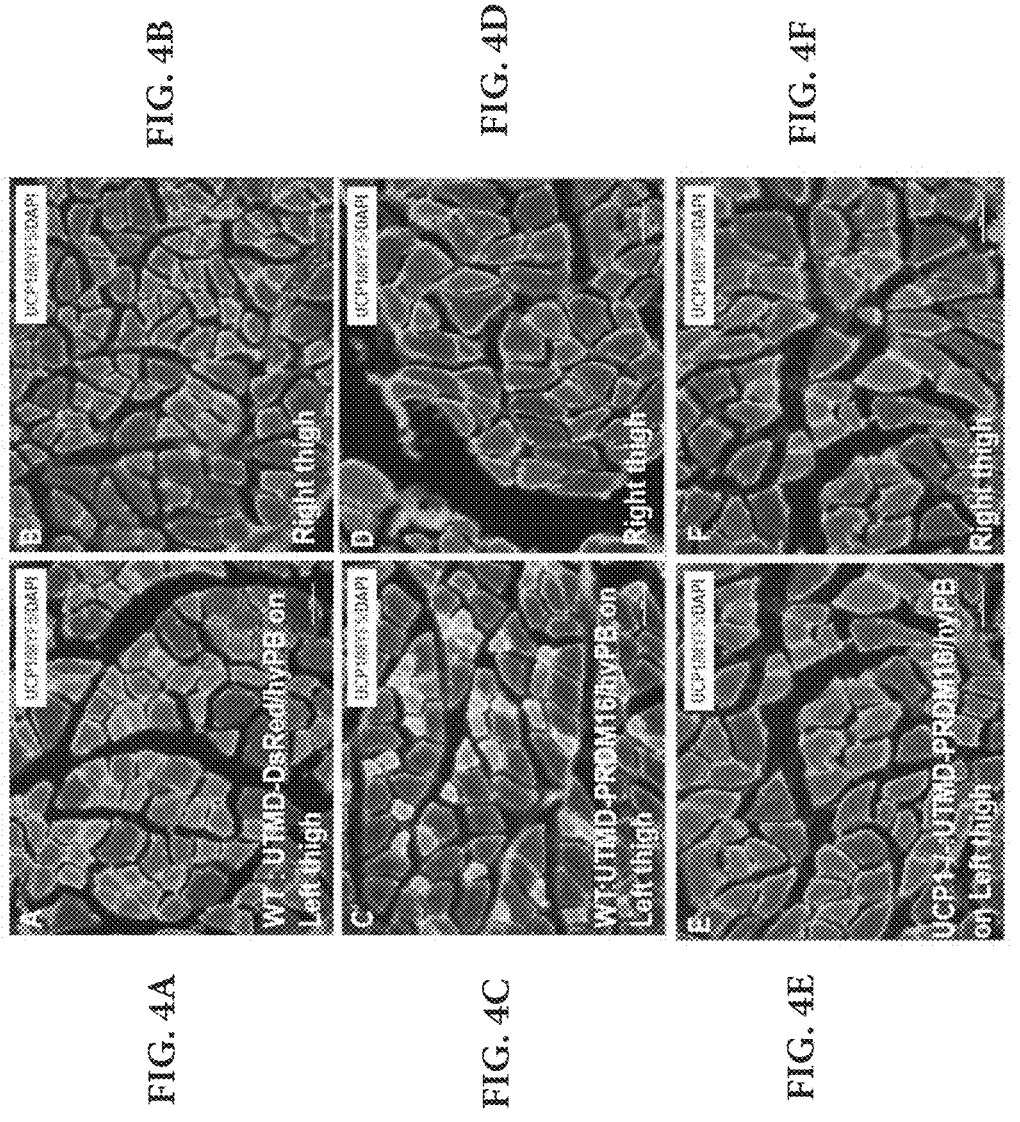
FIGS. 4A-4F are images showing the expression of mUCP1 in adult mice skeletal muscle after UTMD-mediated gene delivery of mUCP1 and PRMD16 genes.
Figure 4G:
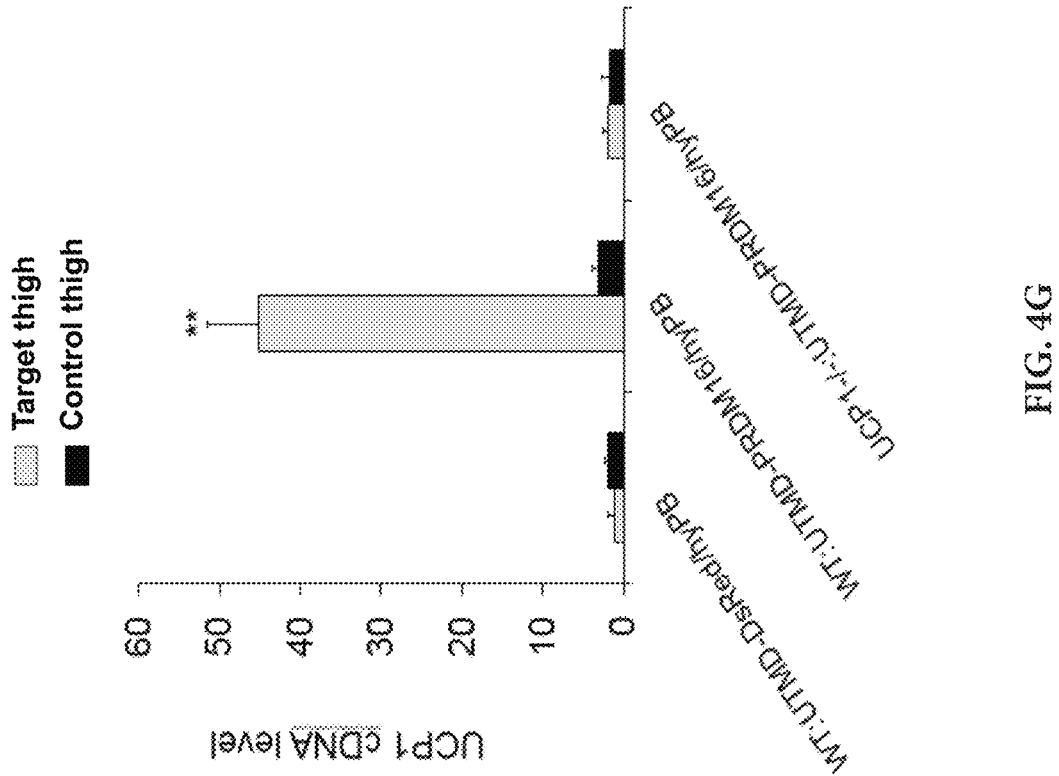
FIG. 4G is a graphical representation of mUCP-1 cDNA levels as measured by quantitative real-time reverse transcription polymerase chain reaction (qRT-PCR) for the samples captured in FIGS. 4A-4F.

FIGS. 4A-4F are images showing the expression of mUCP1 in adult mice skeletal muscle after UTMD-mediated gene delivery of mUCP1 and PRMD16 genes. FIG. 4A is an image showing the lack of mUCP-1 expression in adult mice skeletal muscle after UTMD gene delivery of UTMD-DsRed/hyPB gene plasmids to the left thigh and FIG. 4B is an image also showing the lack of expression of mUCP1 in adult mice skeletal muscle after UTMD-mediated gene delivery of control plasmids to the right thigh in wild type mice. FIG. 4C is an image showing strong expression of mUCP1 in adult mice skeletal muscle after UTMD-mediated gene delivery of UTMD-PRDM16/hyPB gene plasmids to the left thigh and FIG. 4D is an image showing the lack of expression of mUCP1 in adult mice skeletal muscle after UTMD-mediated gene delivery of control plasmid to the right thigh in wild type mice. FIG. 4E is an image showing lack of expression of mUCP1 in adult mice skeletal muscle after UTMD-mediated gene delivery of UTMD-PRDM16/hyPB gene plasmids to the left thigh in mUCP-1 knock-out mice and FIG. 4F is an image showing the lack of expression of mUCP1 in adult mice skeletal muscle after UTMD-mediated gene delivery of control plasmid to right thigh in mUCP-1 knock-out mice. Scale bar is 50 μm. The IHC pattern for protein expression shown in FIG. 3 for the rat model was followed by the mice group showing the presence of mUCP-1 and PRMD16 after the WT group received the PRDM16/hyPB gene therapy (FIG. 4C), also showing negative staining for UTMD-DsRed/hyPB or mUCP-1 in the mUCP-1$^{-/-}$ knock-out mice (FIGS. 4A and 4E). In the mouse model, robust expression of mUCP-1 in wild type mice was observed, but not in m UCP-1$^{-/-}$ knock-out mice after UTMD mediated delivery of pXL-CI-PRDM16/hyPB. IHC from FIG. 4 shows that a mUCP-1 signal only existed in the treated left thigh from WT mice (FIG. 4C) but it was not seen in mUCP-1$^{-/-}$ knock-out mice and right thigh controls (FIG. 4E-D), nor in the controls treated with UTMD-DsRed reporter gene (FIG. 4A). FIG. 4G is a graphical representation of mUCP-1 cDNA levels as measured by quantitative real-time reverse transcription polymerase chain reaction (qRT-PCR) for the samples captured in FIGS. 4A-4F. Values are presented as mean±SEM, n=10 per group; **P<0.001 vs control groups. qRT-PCR results show that mUCP-1 cDNA levels in the treated thigh of the WT mice group after UTMD-pXL-BASII-CI-PRDM16/hyPB was, as expected, 45±4 fold greater than in the thigh of the mUCP-1$^{-/-}$ knock-out mice group (p<0.001). It also showed no difference between expression in treated and control thighs in the mUCP-1$^{-/-}$ knock-out mice (FIG. 4G).

Figures 4H, 4I, 4J, 4K, 4L, 4M:
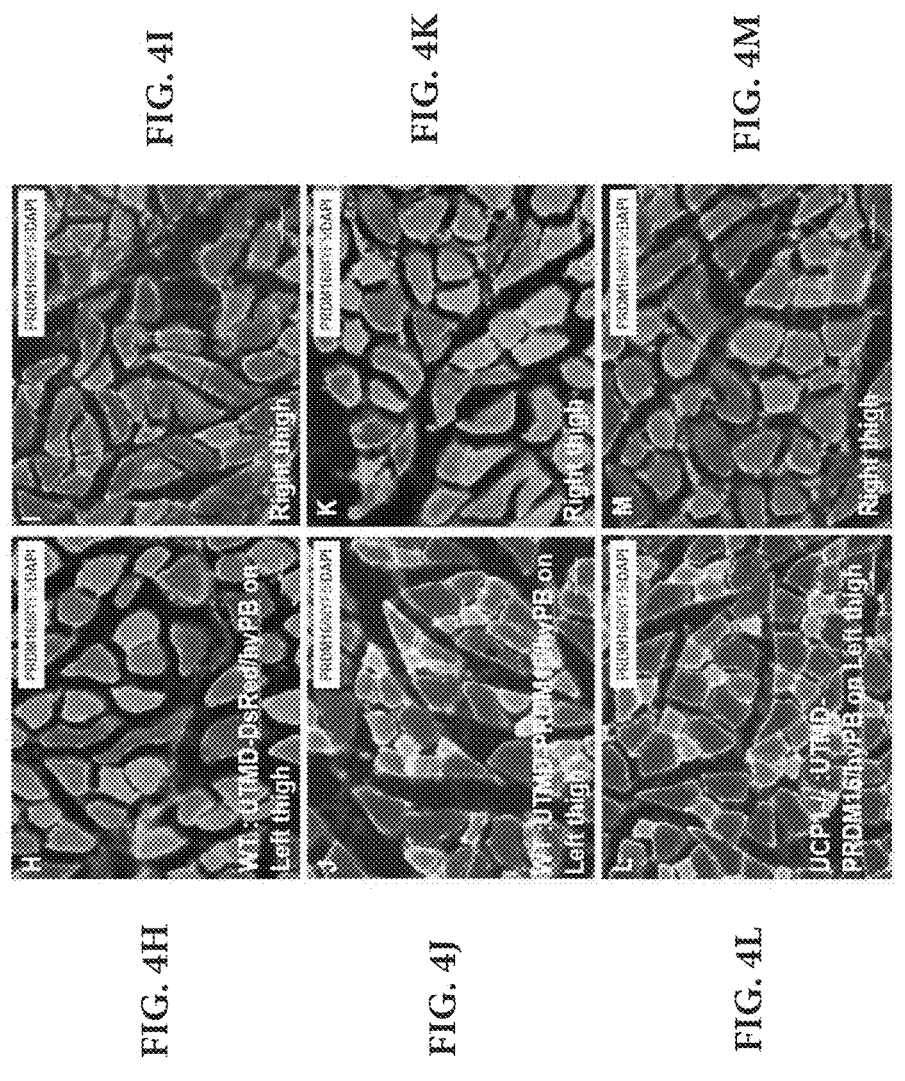
FIGS. 4H-4M are images showing the expression of PRMD16 in adult mice skeletal muscle after UTMD-mediated gene delivery of PRMD16 genes.
Figure 4N:
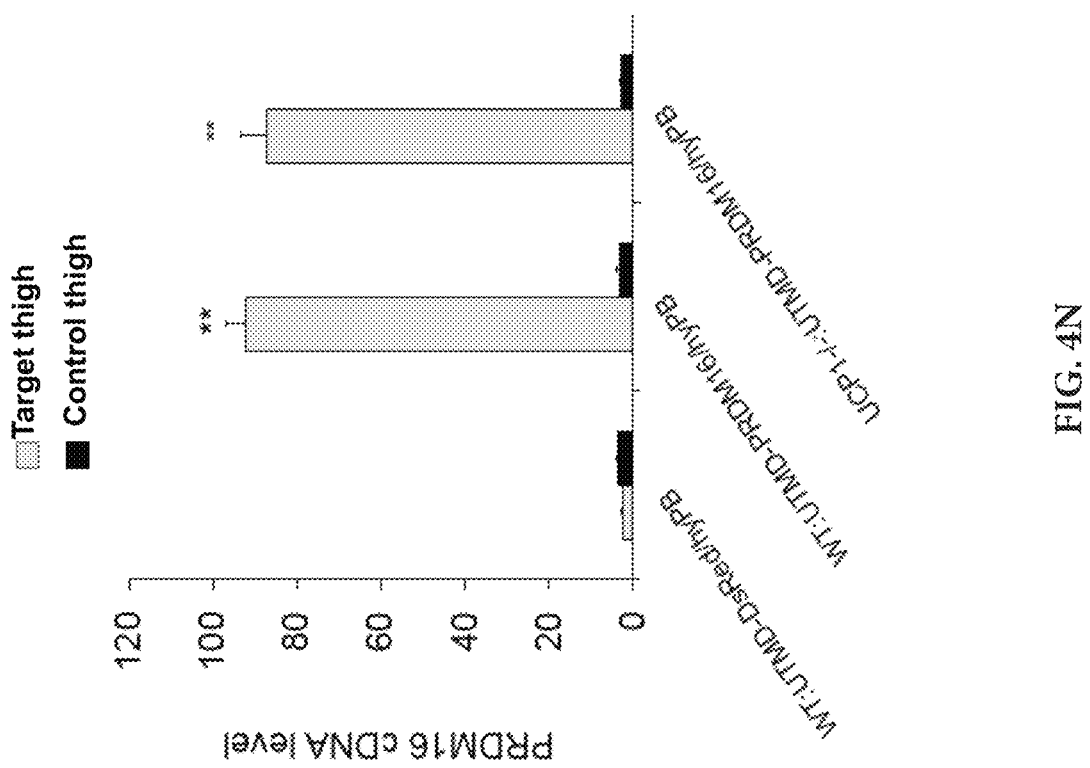
FIG. 4N is a graphical representation of mPRDM16 cDNA levels as measured by quantitative real-time reverse transcription polymerase chain reaction (qRT-PCR) for the samples captured in FIGS. 4H-4M.

Overexpression of PRDM16 was achieved in both the wild type and the UCP-1$^{-/-}$ knock-out mice. FIGS. 4H-4M are images showing the expression of PRMD16 in adult mice skeletal muscle after UTMD-mediated gene delivery of PRMD16 genes. FIG. 4H is an image showing the lack of PRMD16 expression after UTMD gene delivery of UTMD-DsRed/hyPB gene plasmids on left thigh and FIG. 4I is an image showing the lack of PRMD16 expression after UTMD gene delivery of control plasmid to the right thigh in wild type mice. FIG. 4J is an image showing strong expression of PRMD16 in adult mice skeletal muscle after UTMD gene delivery of UTMD-PRDM16/hyPB gene plasmids to the left thigh of wild-type mice. FIG. 4K is an image showing the lack of expression of PRMD16 in adult mice skeletal muscle after UTMD gene delivery of control plasmids to the right thigh in wild type mice. FIG. 4L is an image showing strong expression of PRMD16 in adult mice skeletal muscle after UTMD gene delivery of UTMD-PRDM16/hyPB gene plasmids to the left thigh of a mUCP-1 knock-out mouse and FIG. 4M is an image showing the lack of expression of PRMD16 in adult mice skeletal muscle after UTMD gene delivery of control plasmid to the right thigh of a mUCP-1 knock-out mouse. Scale bar is 50 μm. IHC from FIG. 4 shows that PRDM16 signal only existed in the treated left thigh in WT mice or mUCP-1$^{-/-}$ knock-out mice (FIGS. 4J-L) but are not seen in right thigh controls (FIGS. 4J-L), nor in the controls treated with UTMD-DsRed reporter gene (FIGS. 4K-M). FIG. 4N is a graphical representation of mPRDM16 cDNA levels as measured by quantitative real-time reverse transcription polymerase chain reaction (qRT-PCR) for the samples captured in FIGS. 4H-4M. Values are presented as mean±SEM. n=10 per group; **P<0.001 vs control groups. The qRT-PCR results show that PRDM16 cDNA levels in treated thigh of WT mice or mUCP-1$^{-/-}$ knock-out mice group after UTMD-pXL-BASII-CI-PRDM16/hyPB were 86±5 and 81±7 folds greater, respectively, than in thigh treated with control UTMD-DsRed/hyPB plasmids (p<0.001)(FIG. 4N).

Quantification of the mUCP-1 (FIG. 4G) showed high mUCP-1 levels in the WT but not in the m UCP-1$^{-/-}$ knock-out mice treated with the PRDM16/hyPB gene therapy. These findings were confirmed with Western blotting by measuring PRDM16 and mUCP-1 protein content in the mice biopsy samples after UTMD gene therapy corroborating that the changes in mRNA expression levels resulted in changes in protein content (FIG. 5N).

As shown in FIG. 5, the findings with IHC and molecular measurements (RT-PCR and Western blotting) of perilipin A, a specific marker of adipocytes including brown adipocytes, were evaluated in the skeletal muscles of the treated rodents. Significant overexpression of perilipin A was detected in skeletal muscles. FIG. 5 shows that a remarkable expression of perilipin A was only seen in WT mice but not in UCP-1$^{-/-}$ knock-out mice or DsRed mice after UTMD-pXL-CI-PRDM16/hyPB.

Figures 5A, 5B, 5C, 5D, 5E, 5F:
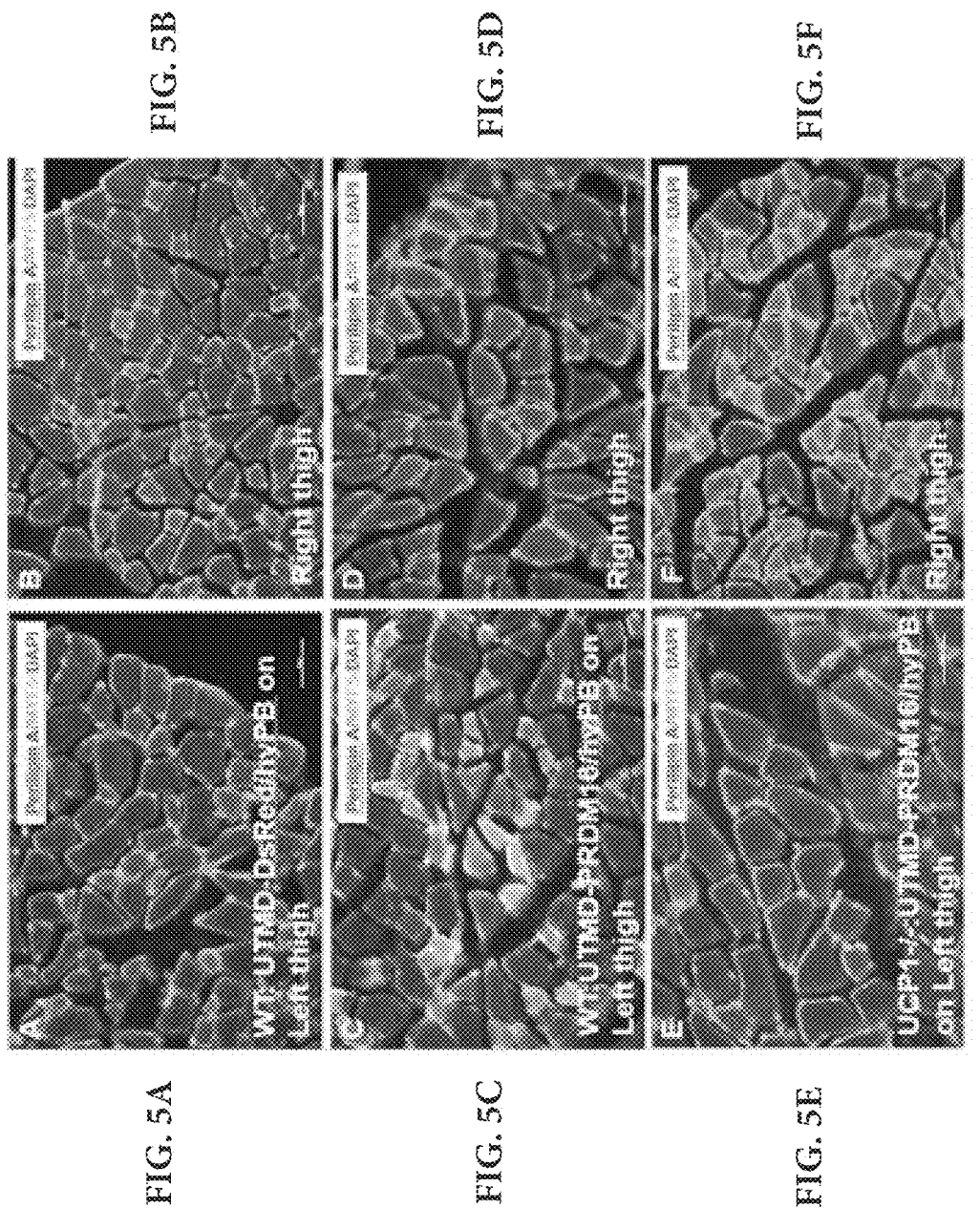
FIGS. 5A-5F are images showing the expression of a brown adipose tissue marker, Perilipin A in adult mice skeletal muscle after UTMD-mediated gene delivery of different nucleic acid constructs.

FIGS. 5A-5F are images showing the expression of a brown adipose tissue marker, Perilipin A in adult mice skeletal muscle after UTMD-mediated gene delivery of different nucleic acid constructs. FIG. 5A is an image showing lack of expression of Perilipin A after UTMD-mediated gene delivery of UTMD-DsRed/hyPB gene plasmids to the left thigh and FIG. 5B is an image showing lack of expression of Perilipin A after UTMD-mediated gene delivery of control plasmid to the right thigh in wild type mice. FIG. 5C is an image showing strong expression of Perilipin A in mice after UTMD-mediated gene delivery of UTMD-PRDM16/hyPB gene plasmids to the left thigh and FIG. 5D is an image showing lack of expression of Perilipin A after UTMD-mediated gene delivery of control plasmid on right thigh in wild type mice. FIG. 5E is an image showing the lack of expression of Perilipin A in mUCP-1 knock-out mice after UTMD-mediated gene delivery of UTMD-PRDM16/hyPB gene plasmids to the left thigh and FIG. 5F is an image showing lack of expression of Perilipin A after UTMD-mediated gene delivery of control plasmid to the right thigh of the mUCP-1 knock-out mice. Scale bar is 50 μm. The perilipin A signal was only identified in the treated left thigh from WT mice (FIG. 5C) but it was not seen in mUCP-1$^{-/-}$ knock-out mice and the right thigh controls (FIGS. 5E-D), nor in the controls treated with UTMD-DsRed reporter gene (FIGS. 5A-B).

Figures 5G, 5H, 5I, 5J, 5K, 5L:
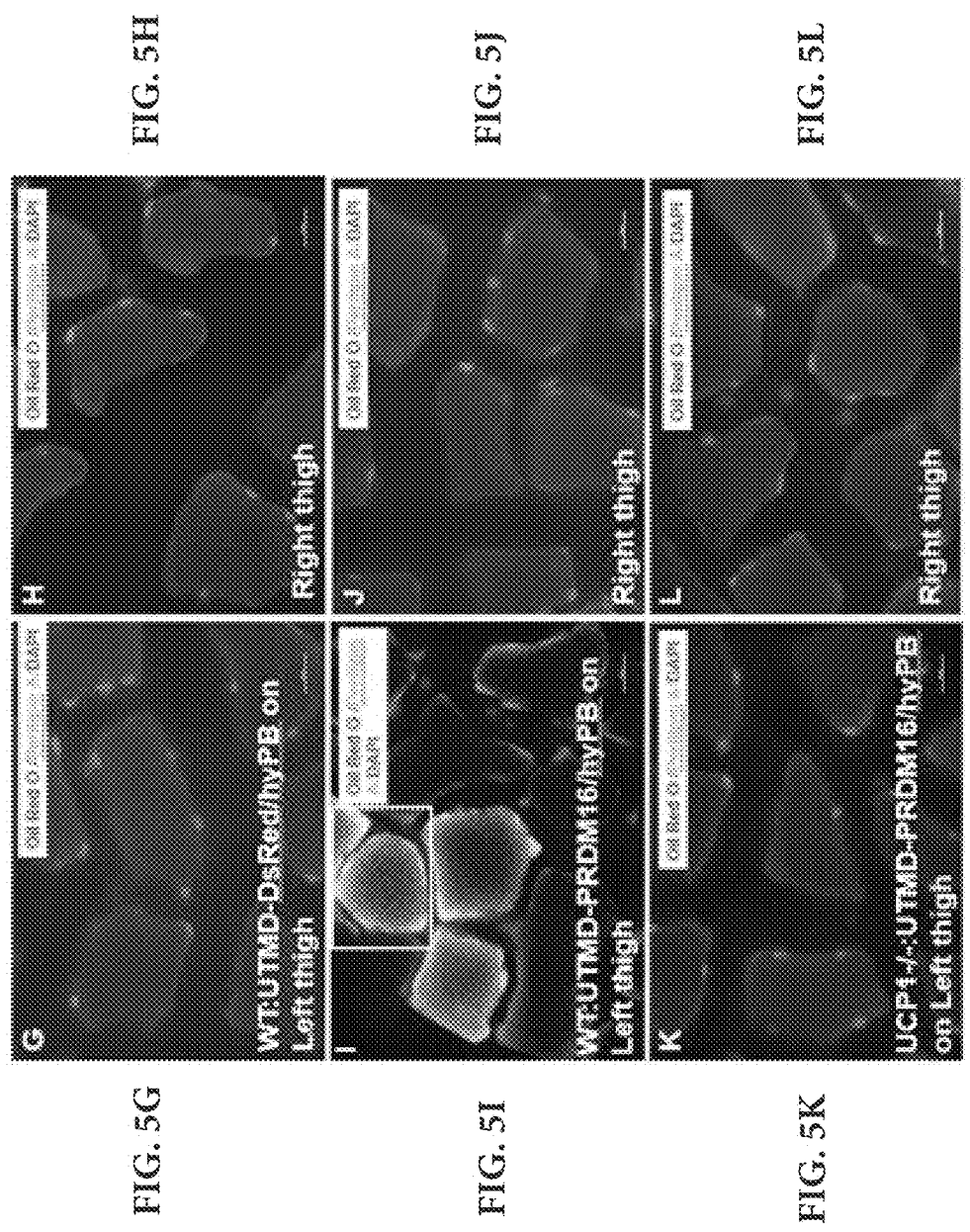
FIGS. 5G-5R are images showing the co-localization of adipose marker, Perilipin A and the neutral lipid dye (oil red O) in adult mice skeletal muscle after UTMD-mediated gene delivery of different nucleic acid constructs.
Figure 5M:
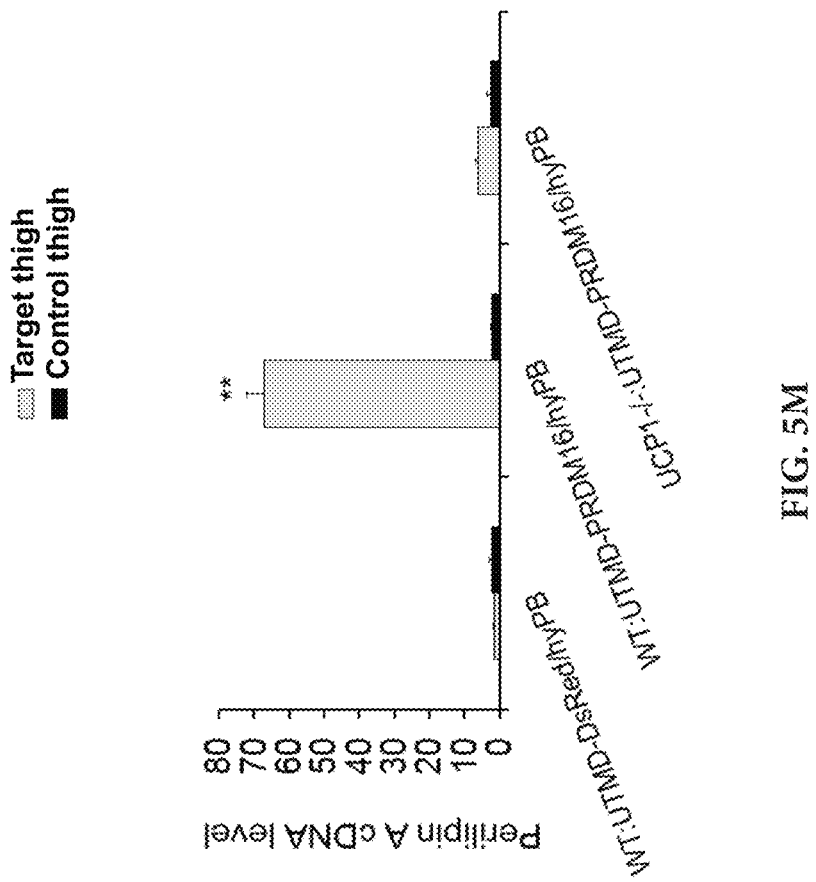
Figure 5N:
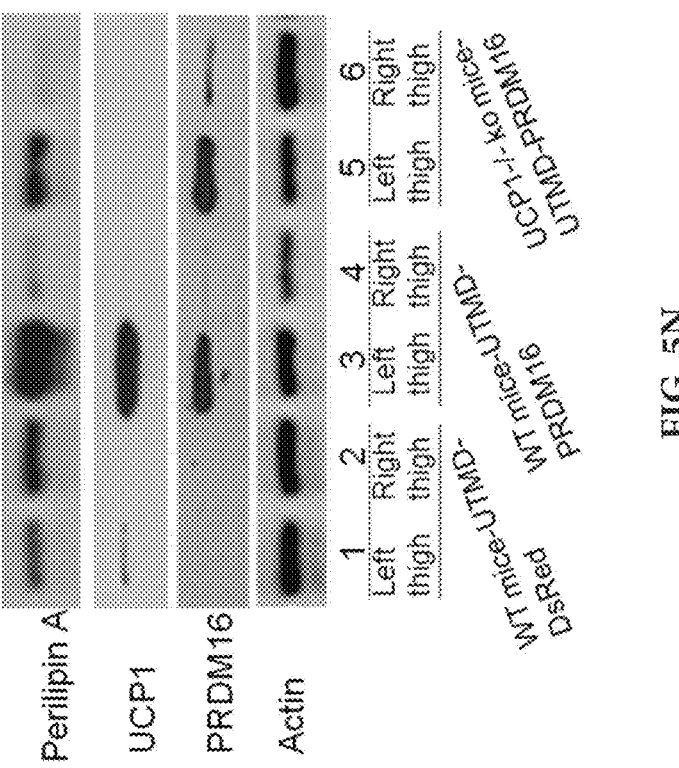

FIGS. 5G-5R are images showing the co-localization of adipose marker, Perilipin A and the neutral lipid dye (oil red O) in adult mice skeletal muscle after UTMD-mediated gene delivery of different nucleic acid constructs. FIG. 5G is an image showing lack of co-localization of adipose marker, Perilipin A and the neutral lipid dye (oil red O) in wild type mice after UTMD-mediated gene delivery of UTMD-DsRed/hyPB gene plasmids to the left thigh and FIG. 5H is an image showing lack of co-localization of adipose marker, Perilipin A and the neutral lipid dye (oil red O) in wild type mice after UTMD-mediated gene delivery of control plasmid to the right thigh. FIG. 5I is an image showing strong co-localization of adipose marker, Perilipin A and the neutral lipid dye (oil red O) in wild type mice after UTMD-mediated gene delivery of UTMD-PRDM16/hyPB gene plasmids to the left thigh and FIG. 5J is an image lacking co-localization of adipose marker, Perilipin A and the neutral lipid dye (oil red O) in wild type mice after UTMD-mediated gene delivery of control plasmid to the right thigh. FIG. 5K is an image lacking co-localization of adipose marker, Perilipin A and the neutral lipid dye (oil red O) in mUCP-1 knock-out mice after UTMD-mediated gene delivery of UTMD-PRDM16/hyPB gene plasmids to the left thigh and FIG. 5L is an image showing lack of co-localization of adipose marker, Perilipin A and the neutral lipid dye (oil red O) in mUCP-1 knock-out mice after UTMD-mediated gene delivery of control plasmid to the right thigh.

FIG. 5M is a graphical representation of Perilipin A cDNA levels as measured by qRT-PCR for the samples captured in FIGS. 5A-5F. Values are presented as mean±SEM, n=10 per group; * P<0.05, **P<0.001 vs control groups. The qRT-PCR results show that Perilipin A cDNA levels in the thigh of the WT mice group treated with UTMD-pXL-BASII-CI-PRDM16/hyPB was 66±5 fold greater, than in right thigh of the WT mice group treated with controls (p<0.001). There was no difference between the thigh treated with UTMD-DsRed/hyPB and thigh treated with controls from the mUCP-1$^{-/-}$ knock-out mice group (FIG. 5M). FIG. 5N is an image of a Western blot analysis detecting expression of PRDM16, mUCP-1, and perilipin A proteins in skeletal muscle. The presence of the Perilipin A and UCP-1 protein in the left thigh of WT mice treated with UTMD-PRMD16 administration shows an intense western blot band. The actin protein western blot band was used as control.

Figures 5O, 5P, 5Q, 5R:
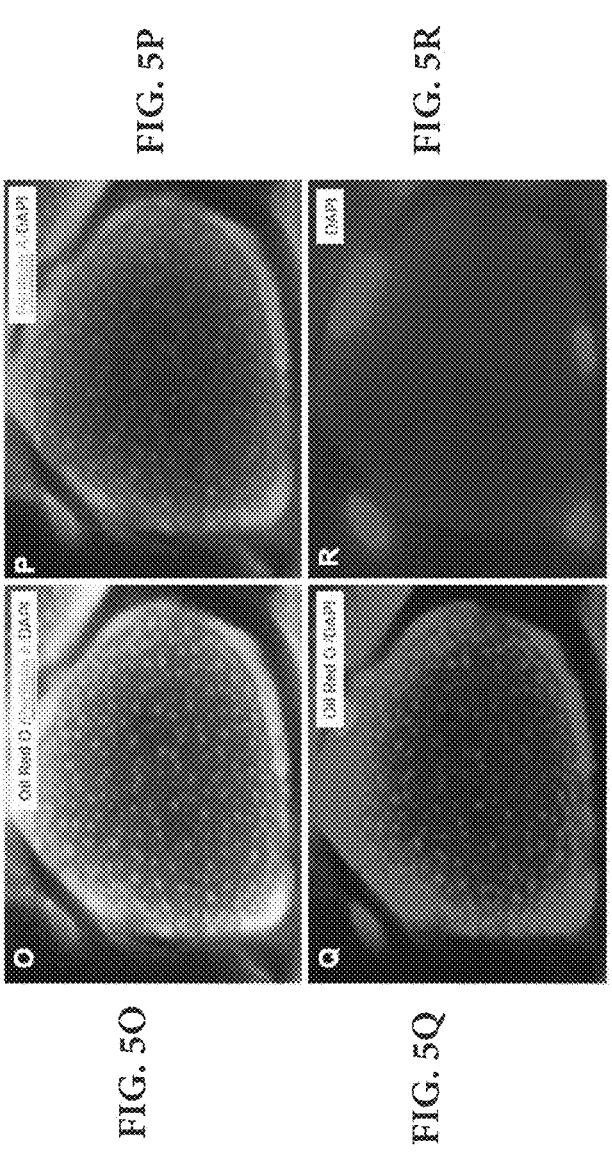

FIGS. 5O-5R are magnified images of cell identified by a square in FIG. 5I, as stained with different agents. Western blotting shows that the perilipin A expression in the left thigh of WT mice was significantly stronger than in UCP-1$^{-/-}$ knock-out mice after treatment with UTMD-pXL-BASII-CI-PRDM16/hyPB gene delivery (FIG. 5R). Perilipin A is an important regulator of lipid storage, and in the studies here, it was co-stained with the neutral lipid dye oil red O. The stained lipid droplets were observed in the skeletal muscles. FIG. 5I clearly shows that neutral lipid droplets and lipid droplet-associated protein (Perilipin A) co-stained in the targeted skeletal muscles area but they are not seen in mUCP-1$^{-/-}$ knock-out mice or right thigh controls (FIG. 5K-5J), nor in the controls treated with UTMD-DsRed reporter gene (FIGS. 5G-5H). FIGS. 5O through 5R are magnified images (white square from panel I) clearly showing tiny lipid droplets in skeletal muscles cells.

There were significant changes in body weight, abdominal subcutaneous fat thickness and weight loss in both rat and mouse models following the UTMD mediated delivery of PRDM16/PGC-1α/BMP7/hyPB gene cocktail and the single gene therapy with the UTMD-PRDM16/hyPB. Initial results indicate that the use of UTMD-based triple gene delivery is more effective than single PRMD16 gene delivery. These data include the apparently higher expression of UCP-1 protein (FIG. 3G vs. 3E) in the triple than in the single, strongly supported by the qRT-PCR measurements (FIG. 3I), and the temperature elevation observed in rats with the administration of the UTMD-PRDM16/PGC-1α/BMP7/hyPB gene cocktail (FIG. 2C).

Disclosed here are methods of treating obesity in a mammal. One such method includes providing a microbubble suspension containing non-viral vectors containing expression cassettes for genes encoding a positive regulatory domain zinc finger protein 16, a peroxisome proliferator-activated receptor gamma coactivator 1-alpha protein, and a bone morphogenetic protein 7 to a subject. This microbubble suspension is introduced into target cells of the subject. Subsequently, the target cells of the subject are exposed to ultrasound to release the non-viral vector containing expression cassettes. The proteins encoded by the expression cassettes are expressed by the target cells to provide effective amounts of positive regulatory domain zinc finger protein 16, the peroxisome proliferator-activated receptor gamma coactivator 1-alpha protein, and the bone morphogenetic protein 7 that are sufficient to increase expression of mitochondrial uncoupling protein. In an embodiment, the target cell is a skeletal muscle cell.

Disclosed here are methods of managing diabetes in a mammal. One such method includes providing a microbubble suspension containing non-viral vectors containing expression cassettes for genes encoding a positive regulatory domain zinc finger protein 16, a peroxisome proliferator-activated receptor gamma coactivator 1-alpha protein, and a bone morphogenetic protein 7 to a subject. This microbubble suspension is introduced into target cells of the subject. Subsequently, the target cells of the subject are exposed to ultrasound to release the non-viral vector containing expression cassettes. The proteins encoded by the expression cassettes are expressed by the target cells to provide effective amounts of the positive regulatory domain zinc finger protein 16, the peroxisome proliferator-activated receptor gamma coactivator 1-alpha protein, and the bone morphogenetic protein 7 to increase expression of mitochondrial uncoupling protein. In an embodiment, the target cell is a skeletal muscle cell.

Brown adipose tissue corresponds to 5-10% of total body weight in mice (20-30 g), 2-5% in 6-month old human babies (150-250 g), and 0.05-0.1% (35-70 g) in an adult male weighing 70 kilograms. Brown adipose tissue is pri-marily and temporarily activated by cold. This activation lasts very shortly. It is not continuous; it's transient but very powerful. Activation means that UCP-1 generates heat by permitting proton influx without ATP synthesis. BAT adipocytes express thermogenin (UCP-1), which catalyzes the re-entry of protons (proton leak) into the matrix, uncoupling the mitochondrial respiratory chain, and consequently generating metabolic heat. Here a hyPBase transposon donor plasmids and helper plasmids in a ratio of 5:1 were used to deliver expression cassettes of PRDM16, PGC-1α, and BMP7. About 1 ml of microbubble suspension containing 2 mg of the plasmids (0.5 ml diluted with 0.5 ml phosphate-buffered solution (PBS)) for a rat or 100 μl of microbubble suspension containing 200 μg plasmids (50 μl of plasmids diluted with 50 μl PBS) for each mouse, infused over 5 min via a pump intravenously (right internal jugular vein). During the infusion, ultrasound was directed to the left thigh using a commercially available ultrasound transducer (S3, Sonos 5500, Philips Ultrasound, Bothell, WA). Ultrasound was then applied in ultraharmonic mode (transmit 1.3 MHz/receive 3.6 MHz) at a mechanical index of 1.4. Four bursts of ultrasound were triggered to every fourth end-systole by electrocardiogram using a delay of 45-70 milliseconds after the peak of the R wave. These settings have shown to be optimal for this embodiment of plasmid delivery by UTMD using this instrument. By an infrared measurement of local left thigh, it was observed that temperature rose from 83° F. to 103° F. (FIG. 2C) roughly corresponding to a temperature increase of 20 OF from UCP-1 activation and metabolic heat production. This temperature increase was sufficient to create a short-term energy gap in both Zucker diabetic rats and wild-type mice and rats.

The metabolic effects of tissue-specific gene therapy directed to overexpression of mUCP-1 was evaluated in the skeletal muscles of obese animals (Zucker rat model—a spontaneous genetic obesity model). Nucleic acid compositions with expression cassettes driving expression of BMP7/PRDM16/PPARGC-1α genes—part of the gene cascade that induces brown adipose tissue differentiation and expression of UCP-1—were delivered to rat skeletal muscles via UTMD. Control animals received plasmids driving expression of genes corresponding to a red fluorescent protein (DsRed). The administration of the gene cocktail to skeletal muscles to animals in this rat model of genetic obesity produced a brown adipose tissue phenotype with mUCP-1 over-expression.

Here, obese Zucker ZDF fa/fa rats were administered plasmid cDNA constructs. These animals exhibit hyperphagia, hyperglycemia, hyperinsulinemia, and hyperlipidemia. These constructs contained expression cassettes of BMP7, PRDM16, and PGC-1α, and were incorporated within microbubbles and intravenously delivered into left thigh of the obese Zucker rats. Control animals received plasmids driving expression of a DsRed reporter gene. An ultrasound transducer was directed to the thigh muscles to disrupt the microbubbles. Intravenous microbubbles carrying plasmids with a cocktail of BMP7/PRDM16/PGC-1α genes were burst within the microcirculation of the left thigh by ultra-sound (treated muscle) in two rats, achieving local gene expression The following observations were made: short-term changes in food consumption, fat mass evaluation with ultrasound image (subcutaneous fat thickness, as well as key metabolic parameters (insulin, glucose, and fatty acids)) between the treated and control obese Zucker rats as a secondary objective. Gene expression for hypothalamic genes involved in energy homeostasis and nutrient-sensing was calculated using the nonparametric Mann-Whitney U (rank-sum) test. Graphics and the statistical analysis were carried out using GraphPad Prism V 6.07. Blood samples were drawn at baseline and after treatment to measure glucose, insulin, and plasma free fatty acids (FFA) levels. The study lasted 30 days with a 20-day period of UTMD gene therapy. Skeletal muscles were harvested from test and control animals for IHC. The results indicated that the plasmid constructs encoding PRDM16, PGC-1α and BMP7 reprogramed adult skeletal muscle tissue into brown adipose cells in vivo.

Figures 6A, 6B, 6C, 6D:
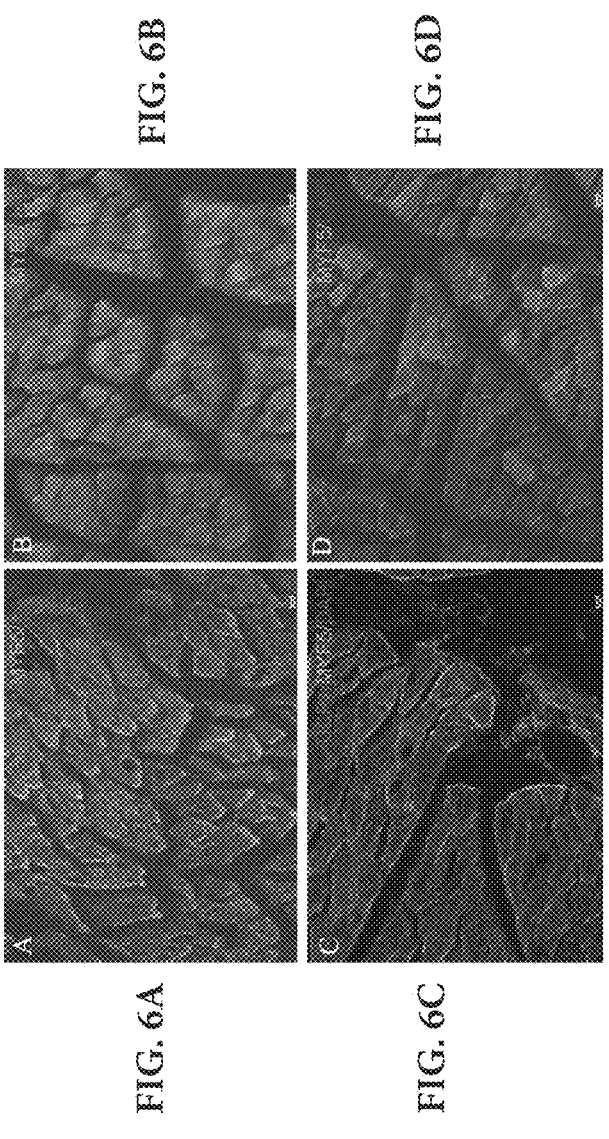
FIGS. 6A-6D are images showing the expression of UCP-1 and Myf5 in muscle tissues of obese Zucker (ZDF-fa/fa) diabetic rats treated with plasmid composition after UTMD-mediated gene delivery of a cocktail of PRDM16, PGC-1a and BMP7 and control plasmids.

IHC analysis was performed using confocal microscopy and FITC-labeled anti-UCP-1, DsRed-labeled anti-Myf5 and anti-perilipin. FIGS. 6A-6D are images showing the expression of UCP-1, Myf5, and perilipin in muscle tissues of rats treated with plasmid composition containing PRDM16, PGC-1α and BMP7 and control plasmids. FIGS. 6A and 6C show robust triple staining for muscle tissue in the left thigh at magnification of 200×, using anti-UCP-1 (red) and anti-Myf5 (green) antibodies in muscle tissues of rats treated with plasmid composition containing PRDM16, PGC-1α and BMP7. Strong detection of UCP-1 expression indicated that the gene combination of PRDM16, PGC-1α and BMP7 reprogrammed adult skeletal muscle into brown adipose cells after UTMD in vivo by day 10 (FIG. 6A) and 20 (FIG. 6C) respectively. FIGS. 6B and 6D show a strong detection of Myf5+(green) and no UCP-1 signal detected in the right thigh of the control rats in muscle tissues of rats treated with control plasmids (magnification at 200×).

Figures 7A, 7B, 7C, 7D:
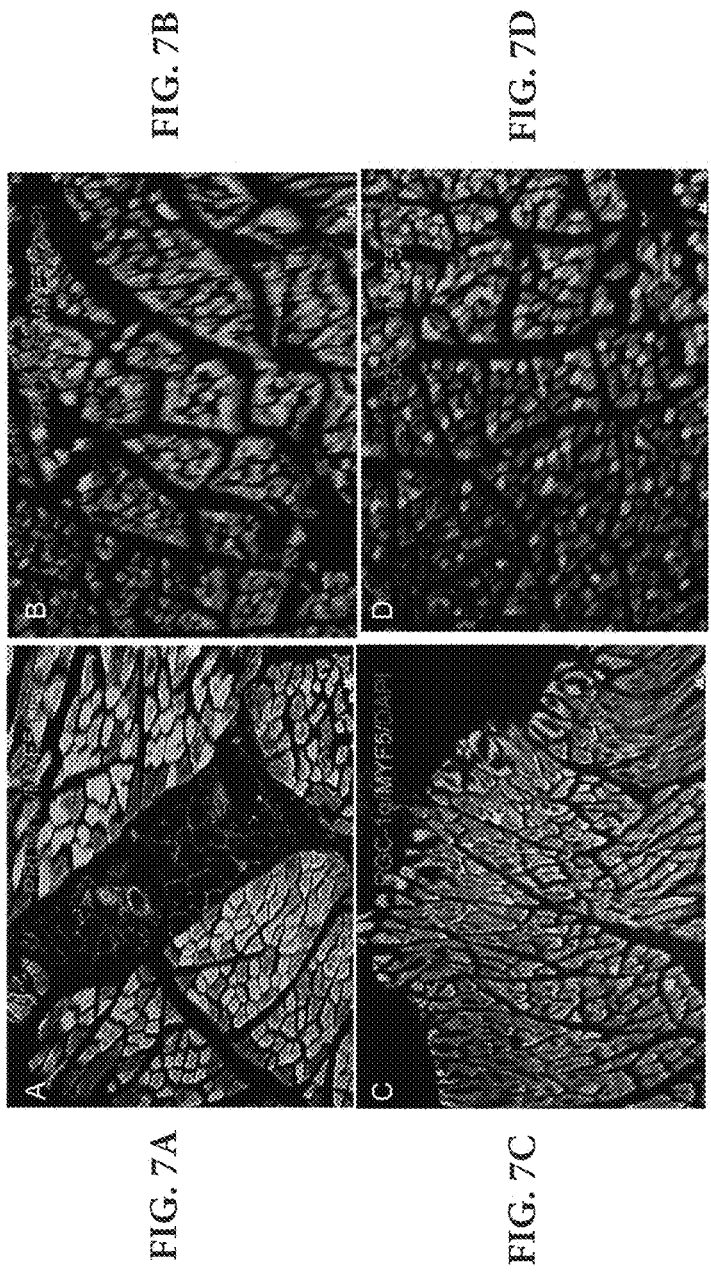
FIGS. 7A (positive staining) and 7B (negative staining) are images showing the expression of PRDM16 in muscle tissues of obese Zucker (ZDF-fa/fa) diabetic rats treated with plasmid composition containing PRDM16, PGC-1a and BMP7 and control plasmids, respectively (anti-PRDM16 (red) and anti-Myf5 (green) antibodies for immunohistochemistry).
FIGS. 7C (positive staining) and 7D (negative staining) are images showing the expression of PGC-1α in muscle tissues of Zucker rats treated with plasmid composition containing PRDM16, PGC-1α and BMP7 and control plasmids, respectively (anti-PGC-1α (red) and anti-Myf5 (green) antibodies for immunohistochemistry).

FIGS. 7A and 7B are images showing the expression of PRDM16 in muscle tissues of rats treated with plasmid composition containing PRDM16, PGC-1α and BMP7 and control plasmids, respectively. FIGS. 7C and 7D are images showing the expression of PGC-1α in muscle tissues of rats treated with plasmid composition containing PRDM16, PGC-1α and BMP7 and control plasmids, respectively. FIG. 7A clearly shows precursors Myf5+ in skeletal muscle cells transdifferentiated into mature brown adipose cells in the muscle of the left thigh in the treated rats. Clear signals for PRDM16 (red) (FIG. 7A) and PGC-1α activity (red) (FIG. 7C) are identified. FIGS. 7B and 7D show no detection of PRDM16 and PGC-1α activity in the muscles of the right thigh of control animals.

Figures 8A, 8B, 8C, 8D:
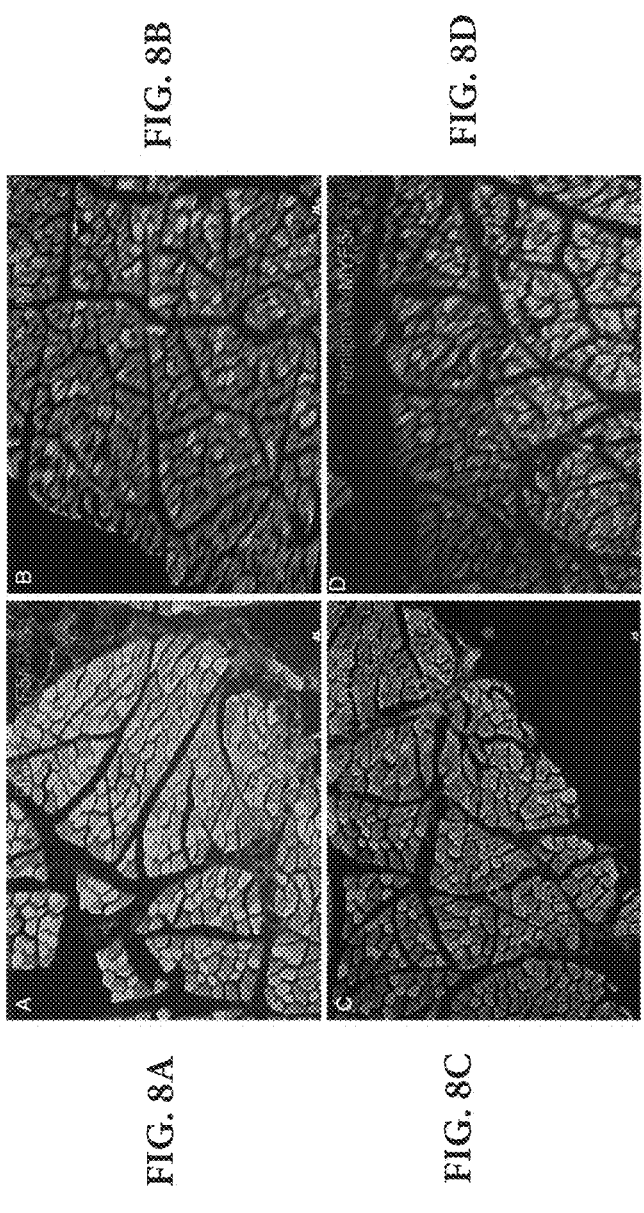
FIGS. 8A (positive staining) and 8B (negative staining) are images showing the expression of BMP7 in muscle tissues of obese Zucker (ZDF-fa/fa) diabetic rats treated with plasmid composition containing PRDM16, PGC-1α and BMP7 and control plasmids, respectively (anti-BMP7 (red) and anti-Myf5 (green) antibodies for immunohistochemistry).
FIGS. 8C (positive staining) and 8D (negative staining) are images showing the expression of perilipin A in muscle tissues of obese Zucker (ZDF-fa/fa) diabetic rats treated with plasmid composition containing PRDM16, PGC-1α and BMP7 and control plasmids, respectively (anti-Perilipin A (red) and anti-Myf5 (green) antibodies for immunohistochemistry).

FIGS. 8A (positive staining) and 8B (negative staining) are images showing the expression of BMP7 in muscle tissues of rats treated with plasmid composition containing PRDM16, PGC-1α and BMP7 and control plasmids, respectively. FIGS. 8C and 8D are images showing the expression of Perilipin A in muscle tissues of rats treated with plasmid composition containing PRDM16, PGC-1α and BMP7 and control plasmids, respectively. FIG. 8C shows the presence of perilipin antibody, a marker of adipose cells, detected at day 20 post UTMD gene delivery in the left thigh of treated rats. There is an absence of activity for perilipin in the muscle of the right thigh in control animals in FIG. 8D.

Figure 9:
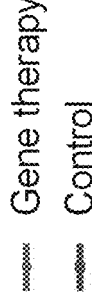
FIG. 9 is a graphical representation of the daily food intake in obese Zucker rats treated with gene therapy constructs containing PRDM16, PGC-1α, and BMP7 and control plasmids, respectively.
Figure 9:
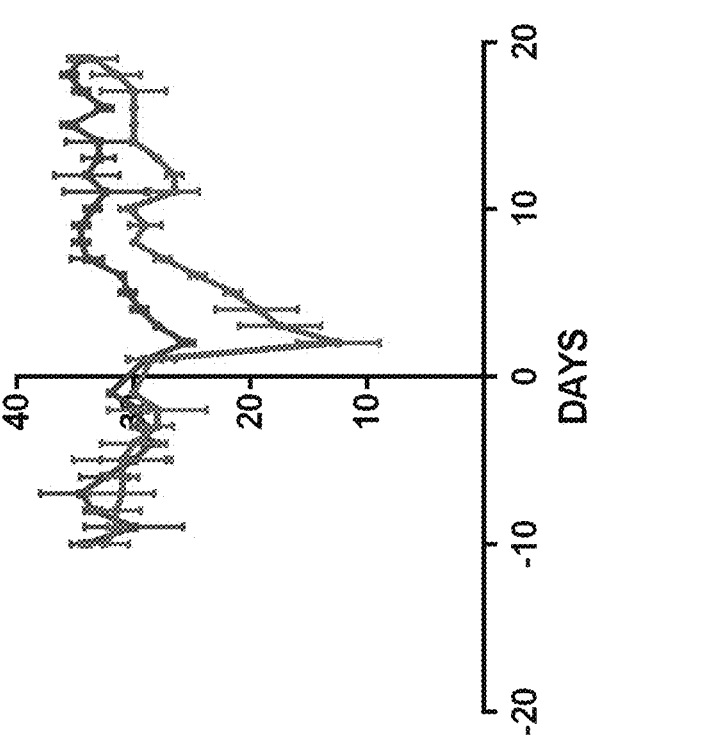

All rats were receiving 132 Kcal/day of regular chow pellets (Harlan rodent diet #2919, 3.3 Kcal/gm). FIG. 9 is a graphical representation of the daily food intake in obese Zucker rats treated with gene therapy construct containing PRDM16, PGC-1α and BMP7 and control plasmids, respectively. Their regular intake before UTMD gene therapy was ~109 Kcal/day. Daily food intake acutely decreased to ~39.6 Kcal/day within the first four days after UTMD gene therapy in the treated rats. These rats under PRDM16, PGC-1α and BMP7 gene therapy administration gradually increased their daily food intake, recovering the intake levels previous to UTMD gene therapy by day 20.

Figure 10:
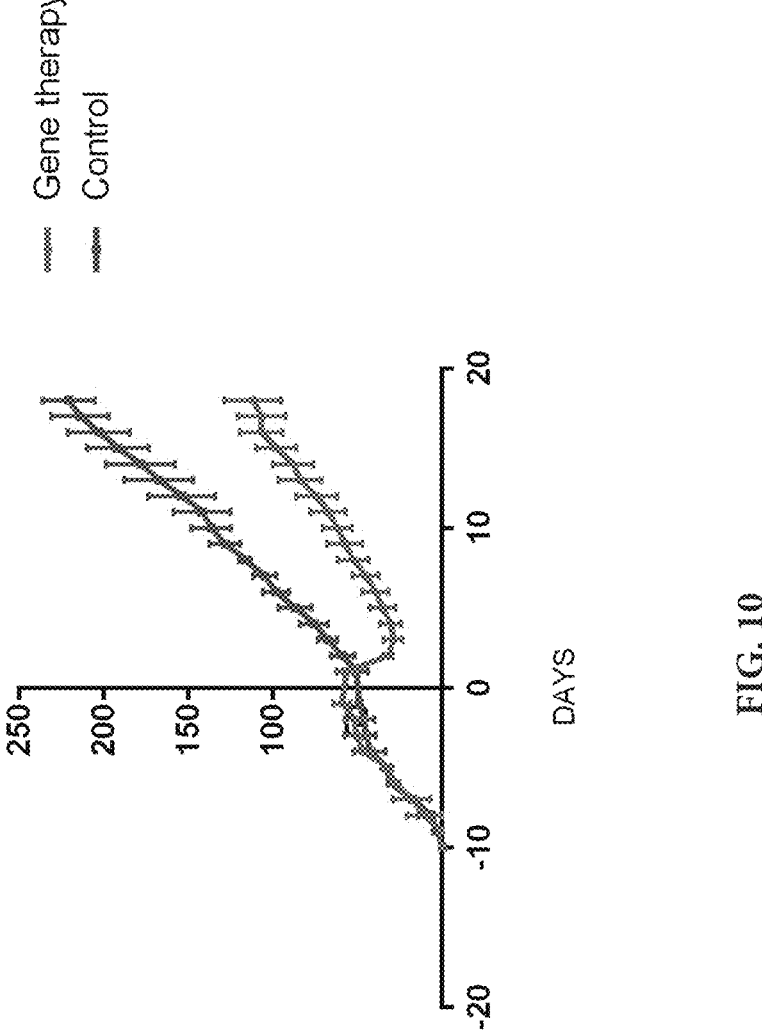
FIG. 10 is a graphical representation of weight gain in the obese Zucker rats treated with gene therapy constructs containing PRDM16, PGC-1α, and BMP7 and control plasmids, respectively.

FIG. 10 is a graphical representation of weight gain in the obese Zucker rats treated with gene therapy construct containing PRDM16, PGC-1α, and BMP7 and control plasmids, respectively. All rats were gaining equal weight previous to UTMD gene therapy as expected (up to ~50 gm). However, the treated rats experienced a sudden weight loss of ~25 gm in the first four days after UTMD gene therapy. Their controls gained ~30 gm within the same period of time. By day 20, treated rats reached a final weight of ~90 gm in spite of having recovered the same amount of food intake previous to UTMD gene therapy administration vs. their controls reaching 225 gm (135 gm difference).

Figure 11:
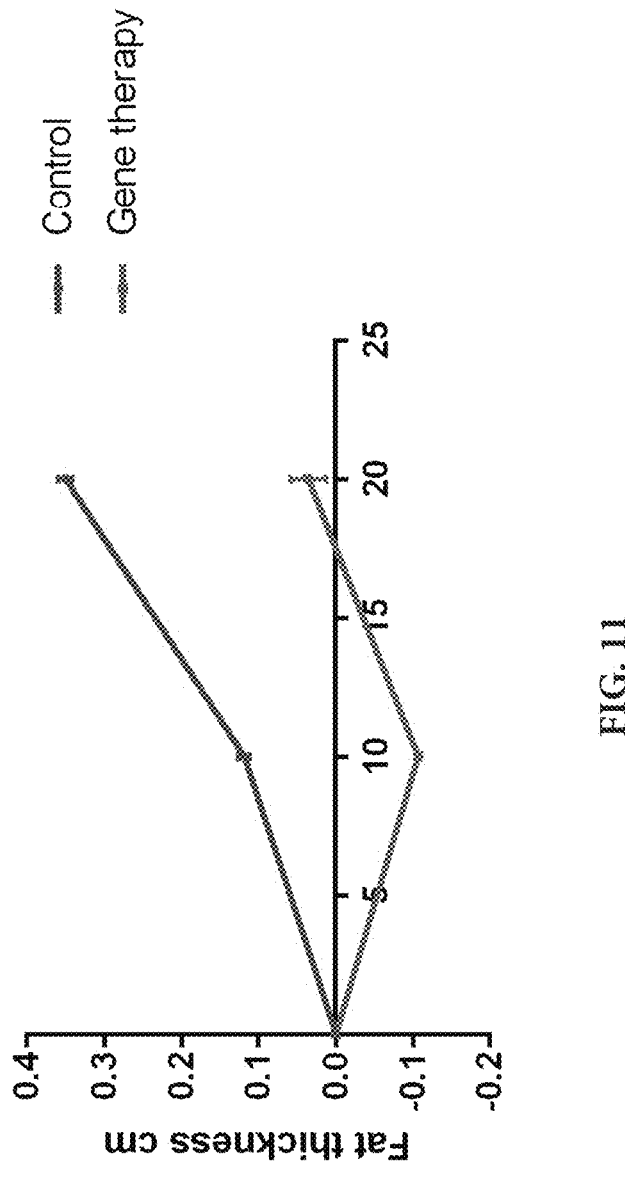
FIG. 11 is a graphical representation of the weight loss, measured in terms of fat thickness, in the obese Zucker rats treated with gene therapy constructs containing PRDM16, PGC-1α, and BMP7 and control plasmids, respectively.

FIG. 11 is a graphical representation of the weight loss, measured in terms of centimeters of fat thickness, in the obese Zucker rats treated with gene therapy construct containing PRDM16, PGC-1α, and BMP7 and control plasmids, respectively. The weight loss from the treated rats as a means of fat thickness evaluated with ultrasound image resulted in a greater percentage from fat mass (loss of −0.1 cm by day 10 and a regain to 0.05 cm by day 20), compared to controls (steady gain of 0.3 cm in 20 days).

Figure 12:
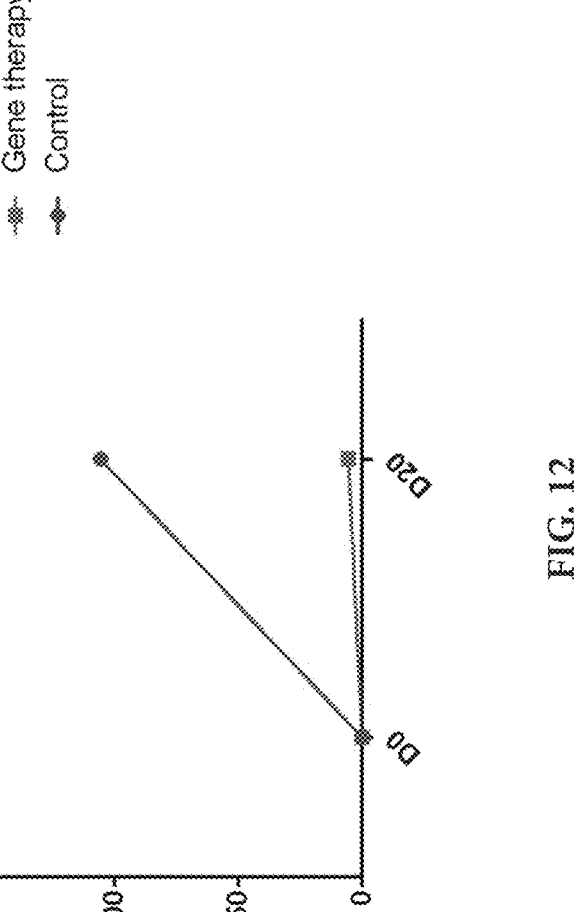
FIG. 12 is a graphical representation of the changes in circulating levels of glucose in the obese Zucker rats treated with gene therapy construct containing PRDM16, PGC-1α, and BMP7 and control plasmids, respectively.

FIG. 12 is a graphical representation of the changes in circulating levels of glucose in the obese Zucker rats treated with gene therapy construct containing PRDM16, PGC-1α, and BMP7 and control plasmids, respectively. The change in glucose circulating levels (Δ) in the non-treated control animals steadily rose up to 100 mg/dl by day 20. The change in blood glucose levels in the treated animals was a low and steady level of ~12.5 mg/dl during the same period of days.

Figure 13:
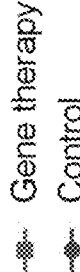
FIG. 13 is a graphical representation of the levels of insulin in the obese Zucker rats treated with gene therapy constructs containing PRDM16, PGC-1α, and BMP7 and control plasmids, respectively.
Figure 13:
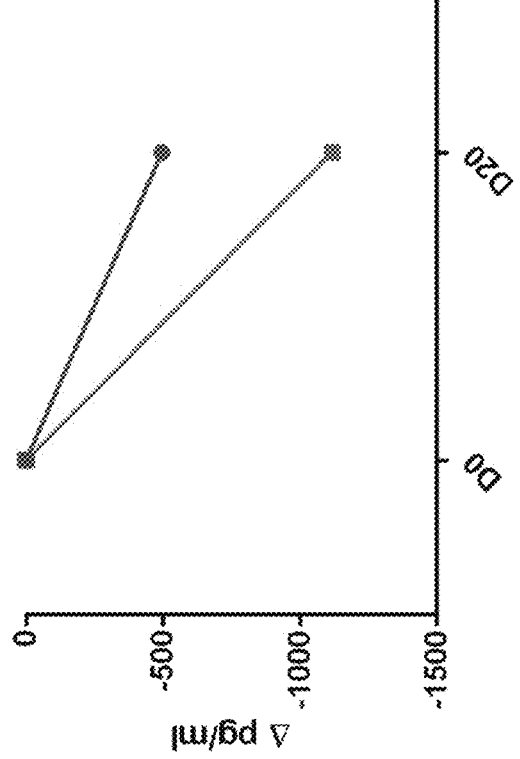

FIG. 13 is a graphical representation of the levels of insulin in the obese Zucker rats treated with gene therapy construct containing PRDM16, PGC-1α, and BMP7 and control plasmids, respectively. The change in insulin levels (Δ) were lower by day 20 (−1250 mIU/L) in the treated rats compared to the change in insulin levels (Δ) (−650 mIU/L) found in the controls.

Figure 14:
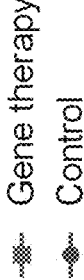
FIG. 14 is a graphical representation of the levels of non-esterified fatty acids (NEFA) in the obese Zucker rats treated with gene therapy constructs containing PRDM16, PGC-1α, and BMP7 and control plasmids, respectively.
Figure 14:
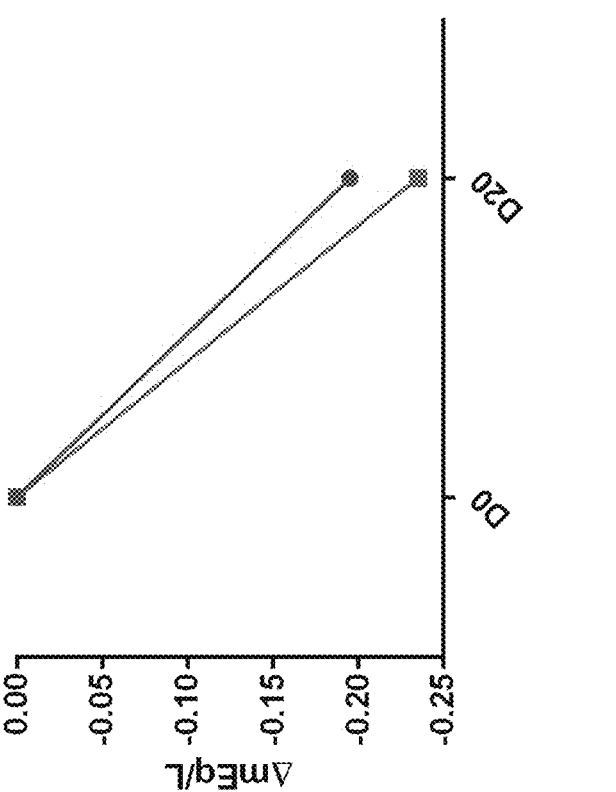

FIG. 14 is a graphical representation of the levels of non-esterified fatty acids (NEFA) in the obese Zucker rats treated with gene therapy construct containing PRDM16, PGC-1α, and BMP7 and control plasmids, respectively. The change in circulating NEFA levels (Δ) followed a similar pattern as insulin levels: −0.15 mEq/L (milliequivalents per liter) in the controls vs. −0.25 mEq/L in the treated rats at day 20.

Figure 15:
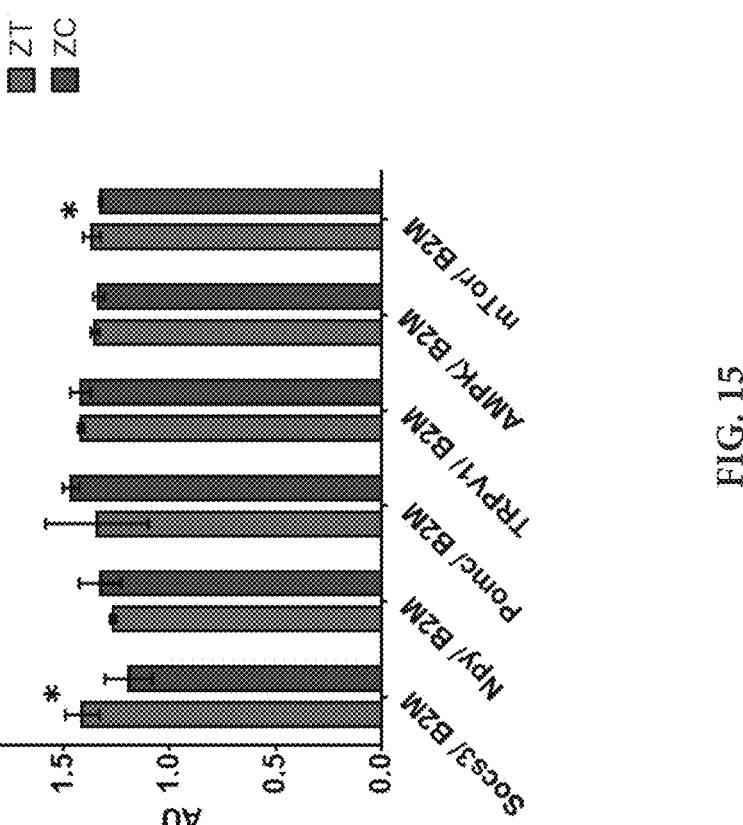
FIG. 15 is a graphical representation showing the pattern of expression of key genes involved in appetite control and nutrient sensing—NPY (neuropeptide Y gene), POMC (proopiomelanocortin), TRPV1 (transient receptor potential cation channel subfamily V member 1), AMPK (5' AMP-activated protein kinase), SOCS3 (Suppressor of cytokine signaling 3), and mammalian target of rapamycin complex (mTOR) in the treated vs the controls animals at day 20.

FIG. 15 is a graphical representation showing the pattern of expression of key genes involved in appetite control and nutrient sensing—NPY (neuropeptide Y gene), POMC iproopiomelanocortin), TRPV1 (transient receptor potential cation channel subfamily V member 1), AMPK (5' AMP-activated protein kinase), SOCS3 (Suppressor of cytokine signaling 3), and mammalian target of rapamycin complex (mTOR) in the treated vs the controls animals. The pattern of expression was obtained from rat brain tissue at day 20. The differential expression of key genes involved in appetite control and nutrient sensing (NPY, POMC, TRPV1, AMPK) were not significant. However, for two key genes the levels of expression was higher in the treated animals (SOCS3 levels of expression in treated 1.4 AU vs controls 1.15 AU, and mTOR 1.3 AU levels in the treated vs 1.2 AU levels in the controls). The slight increase in SOCS-3 and mTOR in the treated animals appears to correlate with the recovery of food ingestion and the more pronounced weight loss, perhaps related to an overwhelming substrate trafficking secondary to the transient UCP-1 over activity in skeletal muscles from days 10 to 20 after UTMD gene therapy. Indeed, recent scientific evidence suggests that circulating substrates (macronutrients such as fatty acids and amino acids) have specific actions to activate receptors and signaling pathways, in addition to providing fuel and essential nutrients. They can exert their effects on target tissues such as the hypothalamus by acting on cell-surface receptors through intracellular signaling cascades or via nuclear receptors to regulate gene transcription.

Effective UTMD-based gene delivery was achieved as shown by enhanced expression of the UCP-1 gene in skeletal muscles (FIGS. 6A and 6C). The data indicate that the systemic gene delivery via UTMD, by increasing local concentration of the transgene BMP7/PRDM16/PGC-1α cocktail (FIGS. 6A-6D and FIGS. 7A-7D), allowed for efficient transfection (via cavitation and tissue pore formation, through ultrasound application and microbubble destruction), and was capable of switching the precursor cell lineage and regulatory myogenic factors for skeletal muscles development into the molecular machinery necessary to establish a terminally differentiated brown adipose tissue and UCP-1 overexpression in vivo. Similar results recently demonstrated that a single UTMD treatment delivered to pancreatic islets of STZ-treated rats with a cell cycle regulation gene cocktail cyclin D2/CDK4/glucagon-like peptide 1 (cyclin D2/CDK4/GLP-1), resulted in durable induction of (3-cell regeneration without evidence of toxicity. Gene therapy by UTMD using the same cell cycle regulation gene cocktail can achieve in vivo evidence of islet regeneration and restoration of (3-cell mass in baboons.

Short-term changes in food consumption, fat mass evaluation with ultrasound image (subcutaneous fat thickness [SFT]), as well as key metabolic parameters (insulin, glucose, and fatty acids) between the treated and the control obese Zucker rats were observed. As shown in the results, the treated rats acutely decreased their daily food intake during the four days following gene therapy administration with the cell cycle regulation gene cocktail, compared to the controls. They gradually recover their food intake patterns to the levels shown previous to UTMD gene therapy. All experimental animals experienced the expected weight gain seen in a Zucker rat before UTMD gene therapy. However, the weight pattern in the treated rats showed a sudden weight loss within the same four days after UTMD gene therapy, unlike their controls which kept gaining weight during the same period of time. Interestingly, the treated rats reached much less weight regain compared with their controls by day 20 in spite of having recovered the same amount of food intake previous to UTMD gene therapy administration (FIGS. 9 and 10). The loss of subcutaneous abdominal fat thickness [SFT] with ultrasound image in the treated Zucker rats was evident when compared with the steady subcutaneous abdominal fat gain shown in the control animals (FIG. 11). The glucose, insulin and NEFA showed low circulating levels in the UTMD gene therapy treated rats after the administration of the UTMD gene cocktail by day 20 when compared to the expected elevated circulating levels of these three biomarkers measured in the control animals in the same day (FIGS. 12, 13, and 14). The functional metabolic result of overexpressing UCP-1 in skeletal muscle correlated with hypophagia, weight loss and metabolic improvement in the treated obese ZDF (fa/fa) rats for a short period of days. By administering the vector-carrying microbubbles containing the cDNA of BMP7/PRDM16/PGC-1α into skeletal muscles, an uncoupling of fatty acid and glucose oxidation from ectopic UCP-1 overexpression may have been enhanced. A localized level of expression of UCP-1 was achieved only in skeletal muscles surrounding the site of the thigh exposed to ultrasound implementation in the treated rats (FIGS. 6, 7, and 8). Therefore, a limited and confined amount ofUCP-1 overexpression in skeletal muscles improved systemic insulin sensitivity, serum lipid parameters and decreased fat mass accumulation, resulting in metabolic improvement of the diabetic phenotype in congenital leptin receptor-deficient ZDF (fa/fa) fatty rats.

The effective amounts of each of the nucleic acid constructs employed in the combination of the lipids-nucleic acid complexes may vary depending on the particular lipid and gas employed, the mode of administration, the condition being treated and the severity of the condition being treated. The effective amounts of each of the nucleic acid constructs may also be adjusted in accordance with other biological factors including age, weight, sex and medical condition of the patient; the severity of the condition to be treated; the route of administration; the renal and hepatic function of the patient; and the particular liposomal components.

EXAMPLES OF METHODS

The following Examples are set forth to aid in the understanding of the various embodiments, and are not intended and should not be construed to limit in any way the embodiments set forth in the claims which follow thereafter.

Example 1

Animal studies were performed according to NIH recommendations and approved protocols of the institutional animal research committee. All phenotypes and molecular techniques (immunohistochemistry, RNA isolation and quantitative RT-PCR analysis and western blotting) were measured in wild type Sprague-Dawley male rats, wild-type (UCP-1$^{+/+}$) and UCP-1-null (UCP-1$^{-/-}$) mice.

The rat model: Wild type Sprague-Dawley male rats at average body weight of 250 grams were purchased from Harlan Laboratories (Indianapolis, Indiana, USA), and housed in a temperature-controlled environment maintained at 30° C. under a 12:12-hour light-dark cycle.

The mouse model: Wild type C57BL/6 mice and Heterozygous for mUCP-1$^{tm1Kz}$ mice were purchased from the Jackson Laboratory (Farmington, Connecticut) and bred to produce wild-type (mUCP-1$^{+/+}$) and mUCP-1-null (mUCP-1$^{-/-}$) mice. Mice were bred and housed at an ambient temperature of 30° C. to prevent thermal stress to the mUCP-1$^{-/-}$ mice. All mice were housed in a temperature-controlled environment maintained at 30° C. under a 12:12-h light-dark cycle. All measurements were conducted at similar times and dates. All in vivo rat and mice studies were performed at the Baylor Scott & White Research Institute (BSWRI), Dallas, TX.

Whole body weights and food intake. Daily weight measurement was performed in the rodents with an Ohaus-Valor 3000 TREME scale. Animals were fed on high fat diets (45% kcal (24 g %) fat; 35% Kcal (41 g %) carbohydrate; 20% Kcal (24 g %) protein) (Cat #D12451, Research Diets Inc., New Brunswick, NJ) before performing UTMD gene delivery. Each animal was kept in individual cages and received the high fat diet chow daily for one month before the study. Food intake was measured on a daily basis.

Subcutaneous Abdominal Fat Thickness Measurement with Ultrasound Image. The thickness of subcutaneous (SQ) adipose tissue was determined by ultrasound image at baseline, day 10 and Day 30 post UTMD. An anatomical area was carefully defined on the left lateral wall of the abdomen. This area was clipped and a reading was obtained with an A-mode device using a S12 transducer with a resonant frequency of 12 MHz (Sonos 5500, Philips Ultrasound, Bothell, WA). The thickness of the subcutaneous abdominal fat layer was then calculated after ultrasonic investigation.

Thermal imaging measurement. Local temperature at both thighs through an infrared imaging technique was measured at baseline, Day 10 and Day 30 post UTMD. All the rats and mice were euthanized 30 days after UTMD. Surface temperature of both thighs was recorded under anesthetized condition using an infrared digital thermographic camera (T660sc, emissivity of 0.98, FLiR Systems) placed 20 cm above the animal. The camera has a thermal sensitivity of ~0.1° C. and a spatial resolution of 640×480 pixels.

Nonviral Site-specific UTMD Gene Therapy. Animals were anesthetized with intraperitoneal ketamine (60 mg/kg) and xylazine (5 mg/kg), and a polyethylene tube (PE 50 for rat, PE 10 for mouse Becton Dickinson, Franklin Lakes, TN, USA) was inserted into the right internal jugular vein by surgical cut down. The hyPB transposon donor plasmids and helper plasmids ratio was 5:1. 1 ml of microbubble suspension containing 2 mg plasmids (0.5 ml diluted with 0.5 ml phosphate-buffered solution (PBS)) for a rat or 100 µl of microbubble suspension containing 200 µg plasmids (50 µl diluted with 50 µl PBS) for each mouse were infused over 5 minutes via pump (Genie, Kent Scientific, Torrington, CT). During the infusion, ultrasound was directed to the left thigh using a commercially available ultrasound transducer (S3, Sonos 5500, Philips Ultrasound, Bothell, WA). Ultrasound was then applied in ultraharmonic mode (transmit 1.3 MHz/receive 3.6 MHz) at a mechanical index of 1.4. Four bursts of ultrasound were triggered to every fourth end-systole by electrocardiogram using a delay of 45-70 ms after the peak of the R wave. These settings have shown to be optimal for plasmid delivery by UTMD using this instrument. Microbubble destruction was visually apparent in all animals. After UTMD, the jugular vein was tied off, the skin closed, and the animals allowed to recover. All animals were euthanized using an overdose of sodium pentobarbital (120 mg/kg). Skeletal muscle tissue was collected from the left (treated) and right (control) thighs (vastus lateralis) in all animals. All samples were placed in weigh boats and delivered to the processing room by the surgical technicians immediately following collection.

Manufacture of Plasmid-Containing Lipid-Stabilized Microbubbles. Lipid-stabilized microbubbles were prepared as previously described. Briefly, a stock solution is prepared containing 270 mg of 1,2-dipalmitoyl-Sn-glycero-3-phosphatidylcholine, (Sigma, St. Louis, MO), 30 mg of 1,2-dipalmitoyl-Sn-glycero-3-phosphatidylethanolamine, (Sigma, St. Louis, MO), and 1 g of glucose. These ingredients were dissolved in a boiling water bath for 20-30 min, with pipetting of contents up and down until no visible particles remain. This stock solution was stored at 4-8° C. Plasmid containing microbubbles were prepared by mixing 2 mg of dried plasmid with 50 µL of lipofectamine 2000 (Invitrogen, Carlsbad, CA) and incubating at room temperature for 15 minutes. This liposome/plasmid DNA mixture was added to 400 µL of lipid stock solution, 50 µL of pure glycerol, and 5 µL of 10% albumin solution, mixed well with a pipette, and then placed in ice. Aliquots of 0.5 mL of this phospholipid—plasmid solution were placed in 1.5 mL clear vials; the air in the headspace of the vials was replaced with perfluoropropane gas (Air Products, Inc, Allentown, PA). Each vial was incubated at 4-8° C. for 30 minutes and then mechanically shaken for 30 seconds by a dental amalgamator (Vialmix™, Bristol-Myers Squibb Medical Imaging, N. Billerica, MA). The mean diameter and concentration of the microbubbles in the upper layer were measured by a particle counter (Beckman Coulter Multisizer III).

Plasmid cDNA Constructs. PRDM16 cDNA (Cat #: 15503, Addgene Company, Cambridge, MA), PGC-1α cDNA (Cat #: 10974, Addgene), BMP7 cDNA (Cat #: sc119058, Ori-Gene Technologies), and DsRed cDNA (Clontech Laboratories) were subcloned into PiggyBac transposon plasmids (pXL-BSII donor plasmid) provided by Dr. Fraser at the University of Notre Dame (Notre Dame, IN, USA), and hyperactive piggyBac™ transposase helper plasmid was provided by Dr. Bradley at Wellcome Trust Sanger Institute (Cambridge, UK). Cloning, isolation and purification of the plasmids were performed by standard procedures, and the PCR products were sequenced to confirm that no artefactual mutations were present.

Immunohistochemistry (IHC). Tissue samples were fixed in 10% formalin for 24 hours and transferred into 70% alcohol for paraffin embedding and 4% paraformaldehyde and 20% sucrose overnight at 4° C. for frozen sections. Cryostat sections of 5-8 m in thickness were further fixed with acetone (−20° C.) for 5 minutes and quenched for 5-20 minutes with 10 mM glycine in PBS. Sections were then rinsed in PBS three times, and permeabilized with 0.5% Triton X-100 in PBS for 15 minutes. The primary antibodies (rabbit polyclonal mUCP-1 antibody, rabbit polyclonal PRDM16 antibody, mouse recombinant monoclonal Myf5 antibody (all from OriGene Technologies, Rockville, MD), and rabbit polyclonal perilipin A antibody (from Abcam Inc, Cambridge, MA)) were added and incubated at 4° C. overnight. After washing with PBS three times for 5 minutes each time, the secondary antibody was added and incubated for 1 hour at room temperature. DAPI (4',6-diamidino-2-phenylindole) (1:5,000 dilution) staining of the samples was performed for 5 minutes. Sections were rinsed three times with PBS for 5 minutes each time and then mounted. The neutral lipid dye oil red O (Sigma, St. Louis, MO) was used in combination with immunofluorescence. Oil red O was applied to the sections for 5 minutes (following 5 minute-washes in PBS). Slides were then rinsed for 30 seconds in double-distilled water followed by a ten-minute wash under cold, slow running tap water. Coverslips were mounted to the dried slides using an anti-fade medium. All IHC presented in the results were representative of protein expression for both mice and rat samples.

RNA isolation and quantitative RT-PCR analysis. Total RNA was isolated from 50 mg of skeletal muscle using the RNeasy mini kit (Qiagen). Real-time quantitative RT-PCR (qRT-PCR) analysis was performed on an ABI 7700 Sequence Detector (Applied Biosystems, Grand Island, NY, USA) using SYBR Green (RT2 SYBR Green qPCR Kit; Qiagen, Boston, MA, USA). Data were normalized to the expression of housekeeping genes (as an endogenous control). Changes in gene expression were normalized to control skeletal muscle samples. Primers were designed and synthesized by IDT Company.

Western blotting. Total protein extracts from skeletal tissue were evaluated with a Cytoplasmic and Nuclei Extraction Kit (Thermo Scientific, Rockford, IL, USA). Protein concentrations were determined using the BCA-200 Protein Assay kit (Pierce, Grand Island, NY, USA); equal amounts of protein were separated by SDS-PAGE to nitrocellulose membranes and incubated with primary antibodies included anti-PRDM16 (1:1,000 dilutions), anti-mUCP-1 (1:2000 dilution), anti-perilipin A (1:2000 dilution), and anti-actin (1:2,000 dilutions). Horseradish peroxidase secondary antibodies were used, and chemiluminescence was determined using the SuperSignal West Dura detection system (Pierce); Cytoplasmic marker (actin) was used to confirm equal loading. All Western blots were performed in duplicate.

Data Analysis. Data were analyzed using Statview software (SAS, Cary, NC, USA). The values are presented as mean±SEM. Differences were analyzed by repeated measures ANOVA with Fisher's post hoc test and were considered significant at $p<0.05$.

Example 2

Experimental animals. Obese Zucker ZDF (fa/fa) male rats were purchased from Charles River Laboratories, housed in a temperature-controlled environment under a 12 hour light-dark cycle, and were fed ad libitum. Animal facilities met the guidelines of the National Institutes of Health (NIH) recommendations and approval of the institutional animal research committee. Animals received regular chow for the length of the study. Two Zucker rats received-pCMV-DsRed plasmid as the control set. Two Zucker rats received the gene cocktail with PRDM16, PGC-1α and BMP7. All genes were delivered as plasmid cDNA. PRDM16 (pcDNA3.1, Catalog no. 15503, deposited by Bruce Spiegelman Lab) and PGC-1α (pcDNA4myc, Catalog no. 10974, deposited by Toren Finkel Lab.) were obtained from the nonprofit plasmid repository Addgene. BMP7 (untagged—human bone morphogenetic protein 7) was purchased from OriGene Technologies (Catalog no. sc119058). Weight measurement was performed in the rats with an Ohaus-Valor 3000 XTREME scale. The thickness of subcutaneous (SQ) adipose tissue was determined by ultrasound image. Food intake was measured on a daily basis.

Manufacture of Plasmid-Containing Lipid-Stabilized Microbubbles. A stock solution was prepared containing 270 mg of 1,2-dipalmitoyl-Sn-glycero-3-phosphatidylcholine (Sigma, St. Louis, MO), 30 mg of 1,2-dipalmitoyl-Sn-glycero-3-phosphatidylethanolamine (Sigma, St. Louis, MO), and 1 g of glucose. These ingredients were dissolved in a boiling water bath for 20-30 minutes, and the contents were pipetted up and down until no visible particles remain. This stock solution was stored at 4° C. Microbubbles containing plasmid constructs were prepared by mixing 2 mg of dried plasmid with 50 µl of Lipofectamine 2000 (Invitrogen, Carlsbad, CA), followed by incubation of this mixture at room temperature for 15 minutes. This liposome/plasmid DNA mixture was added to a mixture of 250 ml of lipid stock solution, 50 ml of pure glycerol, and 5 µl of 10% albumin solution, mixed well, and then placed on ice. Aliquots of 0.5 ml of this phospholipid-plasmid mixture were placed in 1.5 ml clear vials; the air in the headspace of the vials was replaced with perfluoropropane gas (Air Products, Inc, Allentown, PA). Each vial was incubated at 4° C. for 30 minutes and then mechanically shaken for 30 seconds by a dental amalgamator (Vialmix™, Bristol-Myers Squibb Medical Imaging, N. Billerica, MA). The lipid-stabilized microbubbles appear as a milky white suspension floating on the top of a layer of liquid containing the unattached plasmid DNA. The subnatant was discarded and the microbubbles were washed three times with PBS to remove unattached plasmid DNA. The mean diameter and concentration of the microbubbles in the upper layer were measured by a particle counter (Beckman Coulter Multisizer III).

Delivery of plasmid cDNA constructs encoding the gene cocktail with BMP7/PRDM16/PGC-1α into the left thigh of the rats. The microbubbles were delivered by intravenous infusion under anesthesia. The microbubble suspension (containing the BMP7/PRDM16/PGC-1α plasmid constructs) or control solutions (0.5 ml of phospholipid-plasmid solution diluted with 0.5 ml PBS) were infused over 5 minutes using a pump (Genie, Kent Scientific). Plasmid DNA containing the reporter gene DsRed, or the functional gene cocktail construct under the regulation of a cytomegalovirus (CMV) promoter was incorporated within the phospholipid shell of perfluoropropane gas-filled microbubbles. During this infusion, a commercially available ultrasound transducer (S3 probe, Sonos 5500, Philips Ultrasound, Bothell, WA, USA) was directed to the right thigh of the treated and control rats to disrupt the microbubbles within the microcirculation. The probe was clamped in place. Ultrasound was then applied in ultraharmonic mode (transmit 1.3 MHz/receive 3.6 MHz) at a mechanical index of 1.4. Four bursts of ultrasound were triggered to every fourth end-systole by electrocardiogram using a delay of 45-70 milliseconds after the peak of the R wave. These settings have been shown to be optimal for plasmid delivery by UTMD using this instrument. Microbubble destruction was visually apparent in all rats. Blood samples were drawn after an overnight 12 hour fast at baseline and after treatment. Blood glucose levels were measured. Blood insulin and plasma FFA were measured with radioimmunoassay kits (Linco Research). Skeletal muscle samples were harvested for histology from the right thigh (vastus lateralis) in all animals. All samples were placed in weigh boats and delivered to the processing room by the surgical technicians immediately following collection.

Immunohistochemistry. Tissue samples were fixed and processed for IHC. The expression of UCP-1, PRDM16, BMP7, PGC-1α and perilipin from muscle tissue samples was assayed as follows: Cryostat sections 5 m in thickness were fixed in 4% paraformaldehyde for 15 minutes at 4° C. and quenched for 5 minutes with 10 mM glycine in PBS. Sections were then rinsed in PBS three times and permeabilized with 0.5% Triton X-100 in PBS for 10 minutes. Sections were blocked with 10% volume goat serum at 37° C. for 1 h and washed three times with PBS. The primary antibodies (rabbit polyclonal UCP-1 antibody, rabbit polyclonal PRDM16 antibody, rabbit polyclonal BMP7 antibody, rabbit polyclonal PGC-1α antibody, rabbit polyclonal perilipin antibody and mouse recombinant monoclonal Myf5 antibody [OriGene Technologies]) were added and incubated at 4° C. overnight. After washing with PBS three times for 5 minutes each time, the secondary antibody was added and incubated for 1 h at 37° C. Sections were rinsed five times with PBS for 10 minutes each time and then mounted. DAPI (1:5,000 dilution). The images were taken by Leica confocal microscope TCS SP5.

Real Time RT-PCR analysis. Rat brain slices were obtained after euthanasia at the end of the study to perform real time RT-PCR (TaqMan assays, ThrermoFisher Technologies) and detect key hypothalamic genes influencing energy balance (NPY, POMC, SOCS-3) and nutrient-sensing (AMPK, mTOR, TRPV1) utilizing an ABI PRISM 7900 HT sequence detection system (Life Technologies Corporation, Carlsbad, CA).

Subcutaneous abdominal fat thickness measurement with ultrasound image. An anatomical area in all 4 Zucker rats was carefully defined on the left lateral wall of the abdomen. This area was clipped and a reading was obtained with an A-mode device employing a focused transducer with a resonant frequency of 20 MHz (Sonos 5500, Philips Ultrasound, Bothell, WA, USA). The thickness of the subcutaneous abdominal fat layer was then calculated immediately after ultrasonic investigation.

What is claimed is:
1. A pharmaceutical composition, comprising three expression cassettes capable of inducing UCP-1 expression, wherein:

the composition is formulated for delivery to a skeletal muscle cell in a mammal;

a first non-viral nucleic acid construct with a first expression cassette encodes a positive regulatory domain zinc finger protein 16;

a second non-viral nucleic acid construct with a second expression cassette encodes a peroxisome proliferator-activated receptor gamma coactivator 1-alpha protein; and a third non-viral nucleic acid construct with a third expression cassette encodes a bone morphogenetic protein 7.

2. The pharmaceutical composition of claim 1, wherein the pharmaceutical composition is a microbubble suspension formed by mixing a plurality of lipids with a mixture of the first non-viral nucleic acid construct, the second nucleic acid construct, and the third nucleic acid construct.

3. The pharmaceutical composition of claim 1, wherein the pharmaceutical composition is a microbubble suspension of lipid-coated microbubbles containing a gas suitable for ultrasound-targeted microbubble destruction and a mixture of the first non-viral nucleic acid construct, the second nucleic acid construct, and the third nucleic acid construct.

4. The pharmaceutical composition of claim 3, wherein the gas is perfluoropropane.

5. The pharmaceutical composition of claim 2, wherein the plurality of lipids is cationic lipid.

6. The pharmaceutical composition of claim 2, wherein the plurality of lipids includes 1,2-dipalmitoyl-sn-glycero-3-phosphatidylcholine and 1,2-dipalmitoyl-sn-glycero-3-phosphatidyl ethanolamine.

7. A pharmaceutical composition, comprising a non-viral expression vector containing three expression cassettes capable of inducing UCP-1 expression, wherein:

the composition is formulated for delivery to a skeletal muscle cell in a mammal;

a first expression cassette encoding a positive regulatory domain zinc finger protein 16;

a second expression cassette encoding a peroxisome proliferator-activated receptor gamma coactivator 1-alpha protein; and a third expression cassette encoding a bone morphogenetic protein 7.

8. The pharmaceutical composition of claim 7, wherein the non-viral expression vector is a hyperactive piggyBac transposon-based vector.

* * * * *